(12) United States Patent
Newman et al.

(10) Patent No.: US 9,795,647 B2
(45) Date of Patent: Oct. 24, 2017

(54) COMPOSITIONS AND METHODS FOR MODULATING INFLAMMATORY POTENTIAL

(71) Applicant: New Chapter Inc., Cincinnati, OH (US)

(72) Inventors: Robert A. Newman, Surrey, ME (US); Peiying Yang, Sugar Land, TX (US); Paul Schulick, Brattleboro, VT (US)

(73) Assignee: The Procter & Gamble Company, Cincinnati, OH (US)

( * ) Notice: Subject to any disclaimer, the term of this patent is extended or adjusted under 35 U.S.C. 154(b) by 90 days.

(21) Appl. No.: 14/484,320

(22) Filed: Sep. 12, 2014

(65) Prior Publication Data

US 2014/0377387 A1 Dec. 25, 2014

Related U.S. Application Data

(63) Continuation of application No. 12/790,533, filed on May 28, 2010.

(60) Provisional application No. 61/272,130, filed on Aug. 19, 2009, provisional application No. 61/213,334, filed on May 29, 2009.

(51) Int. Cl.
*A61K 36/53* (2006.01)
*A61K 35/60* (2006.01)
*A61K 45/06* (2006.01)

(52) U.S. Cl.
CPC .............. *A61K 36/53* (2013.01); *A61K 35/60* (2013.01); *A61K 45/06* (2013.01)

(58) Field of Classification Search
CPC ..................................................... A61K 36/53
See application file for complete search history.

(56) References Cited

U.S. PATENT DOCUMENTS

| | | | |
|---|---|---|---|
| 4,525,306 A | 6/1985 | Yajima | |
| 5,023,100 A | 6/1991 | Chang et al. | |
| 6,264,995 B1 | 7/2001 | Newmark et al. | |
| 6,387,416 B1 | 5/2002 | Newmark et al. | |
| 6,451,341 B1 | 9/2002 | Deluca et al. | |
| 7,067,159 B2 | 6/2006 | Newmark et al. | |
| 7,070,816 B2 | 7/2006 | Newmark et al. | |
| 7,112,343 B1 | 9/2006 | Shoemake | |
| 7,470,440 B2 | 12/2008 | Newmark et al. | |
| 7,563,462 B2 | 7/2009 | Newmark et al. | |
| 7,622,142 B2 | 11/2009 | Newmark et al. | |
| 7,744,931 B2 | 6/2010 | Newmark et al. | |
| 7,744,934 B2 | 6/2010 | Newmark et al. | |
| 7,931,922 B2 | 4/2011 | Newmark et al. | |
| 8,114,446 B2 | 2/2012 | Newmark et al. | |
| 8,252,345 B2 | 8/2012 | Newmark et al. | |
| 2006/0020007 A1 | 1/2006 | Berlin | |
| 2006/0188607 A1 | 8/2006 | Schramm et al. | |
| 2006/0280776 A1 | 12/2006 | Koide | |
| 2007/0042059 A1 | 2/2007 | Newmark et al. | |
| 2007/0141138 A1 | 6/2007 | Feuerstein et al. | |
| 2008/0058418 A1 | 3/2008 | D'Angelo et al. | |
| 2009/0018186 A1 | 1/2009 | Chen et al. | |
| 2009/0087501 A1* | 4/2009 | Cummins | A61K 36/15 424/729 |
| 2011/0008457 A1 | 1/2011 | Newman et al. | |

FOREIGN PATENT DOCUMENTS

| | | |
|---|---|---|
| AU | 2002313844 | 6/2003 |
| EP | 1842429 A2 | 10/2007 |
| WO | WO 2007/088421 A2 | 8/2007 |
| WO | WO 2009/040676 A2 | 4/2009 |
| WO | WO 2009/150179 A2 | 12/2009 |

OTHER PUBLICATIONS

Rodrigues et al., Chemical composition and extraction yield of the extract of Origanum vulgare from sub- and supercritical CO2. Journal of Agricultural Food Chemistry, vol. 52, No. 10 (2004) pp. 3042-3047.*
Mehta, "Effect of n-3 Polysaturated Fatty Acids on Barrett's Epithelium in the Human Lower Esophagus", The American Journal of Clinical Nutrition, vol. 87, pp. 949-956, 2008.
Hardman, "Omega-3 Fatty Acids to Augument Cancer Therapy", The Journal of Nutrition, vol. 132, No. 11, Suppl. Nov. 1, 2002.
Drbeckl2, "Skin Cancer Forum-Wild Oregano Oil-Skin Cancer Testimonies", Internet Citation May 26, 2008, pp. 106, XP-002593576, URL: http://www.topicalinfo.org/forum//topic.asp?TOPIC_ID=308.
Anonymous, "OxyOrega by NHAS", Internet Citation Mar. 2, 2009, pp. 1-2, URL: http://web.archive.org/web/20090302133851/http://www.taoofherbs.com/products/3317/NorthAmericanHerbSpice/OxyOrega.htm.
Gao et al., "Reversal of Angiogenesis In Vitro, Induction of Apoptosis and Inhibition of Akt Phosphorylation in Edothelial Cells by Thromboxane A2", Circ. Res., vol. 87, No. 27, pp. 739-745, Oct. 2000.
Han et al., "Dietary Polyphenois and Their Biological Significance", Int. J. Mol. Sci., vol. 8, pp. 950-988, 2007.
All Office Actions issued in U.S. Appl. No. 12/790,533, filed May 28, 2010.
Uddhav P. Kelavkar et al. "Prostate Tumor Growth and Recurrence Can Be Modulated by the [omega]-6: [omega]-3 Ratio in Diet: Athymic Mouse Xenograft Model Simulating Radical Prostatectomy", Neo plasia, vol. 8, No. 2, Feb. 1, 2006, pp. 112-124.
Singh, J. et al.: "Dietary Fat and Colon Cancer: Modulation of Cyclooxygenase-2 by Types and Amount of Dietary Fat During the Postinitiation Stage of Colon Carcinogenesis", Cancer Research, American Association for Cancer Research, US, vol. 57, No. 16, Jan. 1, 1997, pp. 3465-3470.
Bartsch, H.: "Dietary polyunsaturated fatty acids and cancers of the breast and colorectum: emerging evidence for their role as risk modifiers", Carcinogenesis, vol. 20, No. 12, Dec. 1, 1999, pp. 2209-2218.

(Continued)

*Primary Examiner* — Kara Johnson
(74) *Attorney, Agent, or Firm* — Amanda Herman; Alexandra S. Anoff

(57) ABSTRACT

This disclosure relates to novel herbal compositions comprising extracts of rosemary and oregano, and methods of using the herbal compositions to modulate inflammatory potential. One or both of the extracts may be supercritical extracts. The disclosure further relates to methods of treating inflammation, rheumatoid arthritis, osteoarthritis, or combinations thereof, using the herbal compositions.

12 Claims, 17 Drawing Sheets

(56) References Cited

OTHER PUBLICATIONS

Hedelin, Maria et al.. "Association of frequent consumption of fatty fish with prostate cancer risk is modified by COX-2 polymorphism", International Journal of Cancer, vol. 120, No. 2, Oct. 25, 2006, pp. 398-405.

Anonymous: "Omega 3 Oils: The Essential Nutrients", Sep. 20, 2001, pp. 1-8, retrieved from Internet: URL: http://web.archive.org/web/20010920145316/http://www.mercola.com/beef/omega3_oil.htm.

Aronson, William J et al. "Modulation of omega-3/omega-6 polyunsaturated ratios with dietary fish oils in men with prostate cancer",Urology, vol. 58, No. 2, Aug. 1, 2001, pp. 283-288.

Anonymous: "Extra Virgin Omega-Rich Fish Oil", retrieved from www.gnpd.com, Nov. 2009.

Anonymous: "New Chapter Wholemega™", Jul. 5, 2009, pp. 1-3, retrieved from Internet: URL:http://web.archive.org/web/20090705023050/http://www.newchapter.com/prdoucts.wholemega.

Bahle, S.D. et al. "Oregano and rosemary extracts inhibit oxidation of long-chain n-3 fatty acids in Menhaden oil", Journal of Food Science, vol. 72, No. 9, Jan. 1, 2007, pp. C504-C508.

Harris, W.S. et al. "The comparative reductions of the plasma lipids and lipoproteins by dietary polyunsaturated fats: Salmon oil versus vegetable oils", Metabolism, Clinical and Experimental, vol. 32, No. 2, Feb. 1, 1983, pp. 179-184.

Chautan, M. et al. "Effects of salmon oil and corn oil on plasma lipid level and hepato-biliary cholesterol metabolism in rats", Biochimica et Biophysica Acta—Lipds and Lipid Metabolism, vol. 1046, No. 1, Aug. 28, 1990, pp. 40-45.

EP Search Report and Written Opinion for 12965D&L (Application No. 15170548.0-1456) dated Oct. 13, 2015.

Fradet, V. et al. "Dietary Omega-3 Fatty Acids, Cyclooxygenase-2 Genetic Variation, and Aggressive Prostate Cancer Risk", Clinical Cancer Research, vol. 15, No. 7, Jan. 1, 2009, pp. 2559-2566.

Funahashi, Hitoshi et al. "Opposing effects of n-6 and n-3 polyunsaturated fatty acids on pancreatic cancer growth", Pancreas, May 2008, vol. 36, No. 4, pp. 353-362.

Frankel, Edwin et al., "Evaluation of Antioxidant Activity of Rosemary Extracts, Carnosol and Carnosic Acid in Bulk Vegetable Oils and Fish Oil and Their Emulsions.", J. Sci. Food Agric., 1996, 72, 201-208.

Jimenez-Alvarez, D. et al. "Antioxidant Activity of Oregano, Parsley, and Olive Mill Wastewaters in Bulk Oils and Oil-in-Water Emulsions Enriched in Fish Oil," Journal of Agricultural and Food Chemistry, 2008, 56, 7151-7159.

Connor, William E. et al., "The Importance of N-3 Fatty Acids in Health and Disease", American Journal of Clinical Nutrition, vol. 71 (supp.) 171S-175S, 2000.

Raventos, M. et al. "Application and Possibilities of Supercritical CO2 Extraction in Food Processing Industry: An Overview", Food Science Technology International, 2007.

Extended European Search Report for counter-part EP Application No. 10781334.7, dated Oct. 31, 2012, 21 pgs.

* cited by examiner

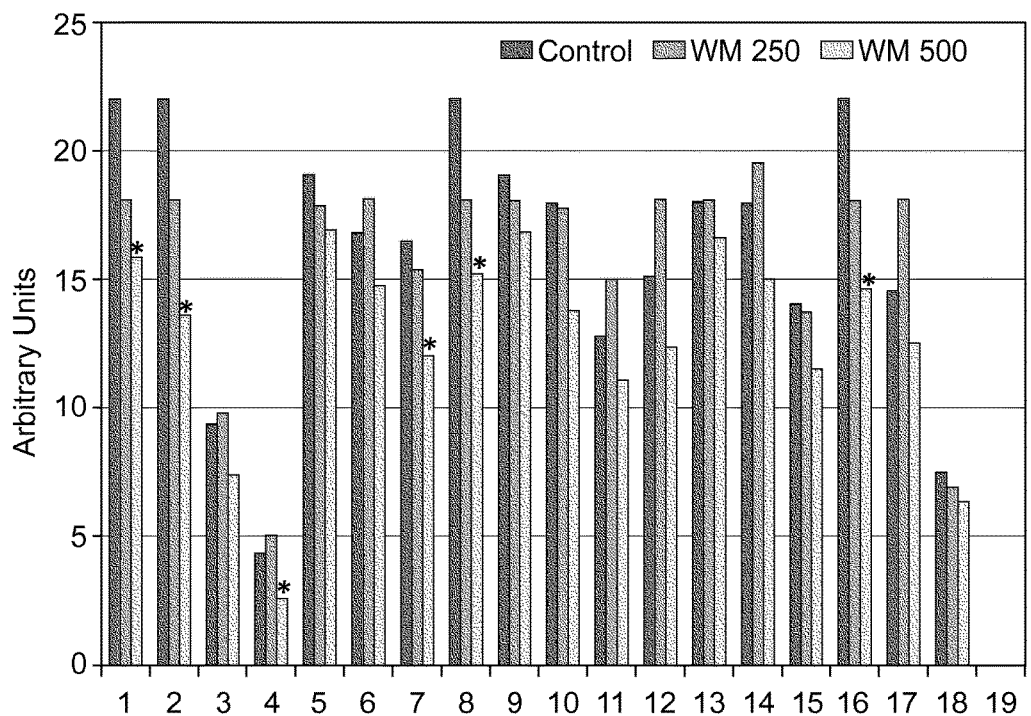

1. alpha-2-macroglobulin
2. adrenergic receptor, beta 2
3. annexin A3
4. acidic ribosomal phosphoprotein PO
5. cysteinyl leukotriene receptor 1
6. hydroxyprostaglandin dehydrogenase 15
7. histamine receptor H2
8. intercellular adhesion molecule 1
9. interleukin 1 receptor
10. leukotriene B4 receptor
11. mitogen activated protein kinase 3
12. phospholipase A2, group V
13. phospholipase C, beta 2
14. phospholipase C, delta 1
15. phospholipase C, gamma 2
16. prostaglandin E receptor 3
17. prostaglandin-endoperoxide synthase 1
18. caspase 1

COMPOSITIONS AND METHODS FOR MODULATING INFLAMMATORY POTENTIAL

CROSS REFERENCE TO RELATED APPLICATIONS

This application is a Continuation of U.S. patent application Ser. No. 12/790,533, filed May 28, 2010; which claims the benefit of U.S. Provisional Patent Application No. 61/213,334, filed May 29, 2009; and No. 61/272,130, filed Aug. 19, 2009; each of which is hereby incorporated by reference in its entirety.

FIELD OF THE INVENTION

The present subject matter relates to a novel herbal composition and methods for modulating inflammatory potential and/or joint health in an animal. In one aspect, the subject matter involves a composition comprising rosemary extract and oregano extract. In a particular embodiment, the extract of rosemary is a supercritical extract. In some embodiments, the extract of oregano is a supercritical extract.

BACKGROUND OF THE INVENTION

Essential fatty acids (EFAs) are naturally occurring unsaturated fatty acids, chain length of 18, 20, or 22 carbon atoms. The predominant natural form of fatty acids is as part of a triglyceride molecule. The triglyceride form generally helps facilitate absorption, storage, and utilization of fatty acids within an organism. Free fatty acids also naturally occur in the body, but to a much lesser extent.

The human body is capable of producing most of the saturated fatty acids which it requires. However, the human body cannot produce all of the unsaturated fatty acids it requires. Although all the EFAs can be found in human food 5 sources, only linoleic and alpha-linoenic acid are considered truly essential, since the body contains enzymes with which it can synthesize all the other EFAs from these two fatty acids. And, while the above is true, the relative ability of human metabolism to form eicosapentaenoic acid (EPA) and docosahexaenoic acid (DHA) is poor at best. This inability is why supplemental dietary oil, such as fish oil, is needed to increase the relative proportion of healthy omega-3 fatty acids in the diet. EPA and DHA constitute the most important so called omega-3 fatty acids. Fish oil is known to be a common source of these omega-3 fatty acids. Additional sources of omega-3 fatty acids also are known, such as, for example, seed oils, plant oils, algal oils and eggs. Epidemiological observations indicate that fish oils and lipid products derived from them produced within the mammalian host reduce platelet aggregation and serum triglycerides which may reduce the risk of myocardial infarction, hypertension, atherosclerosis, and might be involved reducing the risk of certain types of cancer. In addition, it has been shown that EPA and DHA derived from fish oils play important structural roles in membranes of most cells, and influence the fluidity of the cell membranes as expressed by decreased whole-blood viscosity and increased erythrocyte flexibility and deformability.

Moreover, EFAs including EPA and DHA are known precursors of eicosanoids—a class of compounds which includes prostanoids such as prostaglandins and thromboxanes, eukotrienes, and hydroxy fatty acids. Eicosanoids are known to affect platelet aggregation, permeability and tone of the blood vessel walls, blood pressure, and inflammatory immune reactions.

The dietary equilibrium between fatty acids of the n-6 and n-3 series is a significant factor in the regulation of the composition of fatty acids in membranes. In addition, a decreased ratio of n-3 to n-6 dietary fatty acids has been 5 implicated in an increased incidence of health problems, disorders and disease states. The presence of an excess of arachidonic acid (n-6), the precursor of the series 2 eicosanoids, or an excess of its precursor, linoleic acid (n-6), may lead to an increase in thrombogenesis, a decrease in bleeding time, an increase in the inflammatory response of polymorphonuclear monocytes and leukocytes, as well as an increase in smooth muscle reactivity to allergies. In contrast, a diet predominantly based on long chain polyunsaturated fatty acids (PUFAs) of the n-3 series, such as the diet of the fish-eating populations, produce an small increase in bleeding time, and a low incidence of cardiovascular disease, such as, atherosclerosis, arthritis, asthma and other diseases. This is due in-part to the fact that these long chain PUFAs of the n-3 series are the precursors for the series 3 eicosanoids.

One of the primary goals in consuming fish oils is to have important constituents found in them become incorporated into tissue membranes where they serve to modulate cell signal events (e.g. reduce inflammation) and increase membrane fluidity. When cells are activated to release fatty acids from their membranes through the action of phospholipases to form eicosanoids, EPA and DHA compete with arachidonic acid for the COX and LOX enzymes. While released arachidonic acid gives rise to inflammatory prostaglandin products (e.g. PGE2), fish oil lipids produce prostaglandins and lipoxygenase products (e.g. PGE3 and LTBs) that are significantly less prone to cause inflammation than are the AA (Arachidonic acid)-derived products (e.g. PGE2 and LTB4) Furthermore, some molecules known as resolvins and protectins are formed exclusively from fish oil derived polyunsaturated lipids EPA and DHA. These newly discovered products orchestrate inflammation resolution.

Much progress has been made in the early diagnosis and treatment of cancers such as prostate, breast, and lung cancer, and in the treatment and prevention of cardiovascular disease. However, cardiovascular disease and cancer remains the leading causes of disease-related deaths in the United States. There remains a need for new dietary supplements that will improve the beneficial lipid metabolism and promote incorporation of polyunsaturated lipids into biochemical pathways and biological membranes. Such supplements would thereby promote beneficial health consequences, including, for example, improving cardiovascular health and/or treating or preventing the onset of cell proliferation diseases and disorders, such as cancer.

Applicants have unexpectedly found a new herbal composition that provides significantly enhanced uptake and metabolism of select beneficial polyunsaturated lipids and improved consequences for health benefits.

SUMMARY OF THE INVENTION

In some aspects, the invention relates to a composition for oral administration. The composition may comprise a supercritical extract of rosemary. The composition may comprise a supercritical extract of oregano. The composition may comprise the extracts in amounts sufficient to modulate inflammatory potential in a mammal. The composition may be in the form of one or more capsules, tablets, or pills. The composition may comprise a carrier, such as a carrier selected from the group consisting of magnesium carbonate, magnesium stearate, talc, sugar, lactose, pectin, dextrin, starch, gelatin, tragacanth, methylcellulose, sodium carboxymethylcellulose, a low melting wax, cocoa butter, and combinations thereof.

The composition may comprise an additional agent, such as an agent selected from the group consisting of antineoplastic agents, antioxidants, growth inhibiting agents, herbal extracts, nutrients, and combinations thereof. The supercritical extract of rosemary may be a supercritical extract of a leaf of rosemary. The supercritical extract of oregano may be a supercritical extract of a leaf of oregano. The composition may be administered in two or three doses daily. The composition may comprise about 0.001 mg to about 100 mg per kilogram of body weight of active ingredient compounds. The composition may comprise a therapeutically effective amount of supercritical extracts of rosemary and oregano to treat inflammation, rheumatoid arthritis, osteoarthritis, or combinations thereof.

In some aspects, the invention relates to a composition for oral administration comprising a supercritical extract of leaf of rosemary. The composition may comprise an extract of oregano. The composition may comprise an extract of rosemary and an extract of oregano in amounts sufficient in combination to modulate inflammatory potential in a mammal. The extract of oregano may be obtained by solvent-based extraction. The composition may be administered in two or three doses daily. The composition may comprise between 200 mg per day and 2000 mg per day of active ingredient compounds per kilogram of body weight.

The composition may comprise a therapeutically effective amount of supercritical extract of rosemary and extract of oregano to treat inflammation, rheumatoid arthritis, osteoarthritis, or combinations thereof. The composition may further comprise a carrier, such as a carrier selected from the group consisting of magnesium carbonate, magnesium stearate, talc, sugar, lactose, pectin, dextrin, starch, gelatin, tragacanth, methylcellulose, sodium carboxymethylcellulose, a low melting wax, cocoa butter, and combinations thereof. The composition may comprise an additional agent, such as an agent selected from the group consisting of antineoplastic agents, antioxidants, growth inhibiting agents, herbal extracts, nutrients, and combinations thereof.

In some aspects, the invention relates to a method of maintaining joint health in a mammal. The method may comprise providing the mammal with a composition as disclosed herein.

BRIEF DESCRIPTION OF THE DRAWINGS

FIG. 20. Inflammation gene array expression in RAW macrophage cells treated with WholeMega. The designation (*) denotes a level of expression reduced by more than 20% due to WholeMega. The expression of receptor or enzymes associated with COX and 5-LOX as well as phospholipase in RAW cells were reduced in comparison to that of untreated control cells.

DETAILED DESCRIPTION OF THE INVENTION

Definitions

Figure 1:
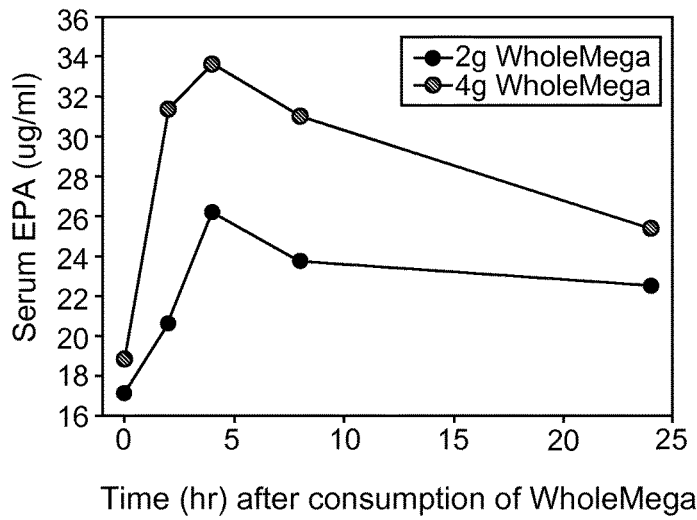
FIG. 1. Consumption of one exemplary composition of the present subject matter (indicated as "WholeMega" herein with reference to the Figures) 2 g or 4 g/day) produces easily detectable serum levels of EPA (representative fish oil derived omega-3 PUFA). The concentration of EPA in the serum correlates with the amount consumed.

As used herein, the terms "administer," "administering," and "administration," refer to any method which, in sound medical practice, delivers the composition to a subject in such a manner as to provide a therapeutic effect.

The phrase "derivative" as used herein refers to any hydrate, solvate, salt, racemate, isomer, enantiomer, prodrug, metabolite, ester, chemical compound or other analog or derivative of a particular chemical compound or molecule. The term "derivative" may also mean a modification to the disclosed compounds, including, but not limited to, hydrolysis, reduction, or oxidation products, of the disclosed compounds. Hydrolysis, reduction, and oxidation reactions are known in the art.

The term "modulating" refers to the process of producing an effect on biological activity, function, health, or condition of an organism in which such biological activity, function, health, or condition is maintained, enhanced, diminished, or treated in a manner which is consistent with the general health and wellbeing of the organism. The term "enhancing" the biological activity, function, health, or condition of an organism refers to the process of augmenting, fortifying, strengthening, or improving.

As used herein, the phrases an "effective amount" or a "therapeutically effective amount" of an active agent or ingredient, or pharmaceutically active agent or ingredient, which are synonymous herein, refer to an amount of the pharmaceutically active agent sufficient enough to have a therapeutic effect upon administration. A therapeutically effective amount of the pharmaceutically active agent may, will, or is expected to cause a relief of symptoms. Effective amounts of the pharmaceutically active agent will vary with the particular condition or conditions being treated, the severity of the condition, the duration of the treatment, the specific components of the composition being used, and like factors.

The term "enhancing" the biological activity, function, health, or condition of an organism refers to the process of augmenting, fortifying, strengthening, or improving. The term "eicosanoid" refers to any of the class of compounds derived from polyunsaturated fatty acids, such as derived from arachidonic acid and linoleic acid. Eicosanoids derive from either omega-3 (w-3) or omega-6 (w-6) EFAs. The w-6 eicosanoids are generally pro-inflammatory; w-3's are much less so. There are four families of eicosanoids: the prostaglandins, the prostacyclins, the thromboxanes, and the leukotrienes. For each, there are two or three separate series, derived either from a w-3 or w-6 EFA. These series' different activities have been correlated with certain health effects of w-3 and w-6 fats. Compositions of the present subject matter may also modulate the physiological effects described herein by modulating the production or metabolism of resolvins and protectins formed from polyunsaturated lipids EPA and DHA.

The term "oxygenase" refers to any of the class of enzymes that catalyze the incorporation of molecular oxygen into its substrate.

The term "supercritical gas" or "supercritical fluid" as used herein refers to a gas is that heated to a temperature critical point, over which the gas will maintain its gaseous state and not turn to a liquid regardless of pressure. A gas heated to a temperature above its critical point will become very dense on compression, so that its characteristics resemble those of a fluid, but will become liquid. Carbon dioxide is commonly used in applications requiring a supercritical fluid. The general properties of supercritical fluids and the general use of supercritical fluids in extraction processes are described in, e.g. Taylor, Supercritical Fluid Extraction, Wiley, 1996; McHugh and Krukonis, Supercritical Fluid Extraction: Principles and Practice, 2nd ed., ButterworthHeinemann, 1994; and Williams and Clifford, Supercritical Fluid Methods and Protocols, Humana Press, 2000, the contents of which are incorporated by reference herein.

Applicants have developed a mixture comprised of herbal extracts mixed together with polyunsaturated oil. In a preferred embodiment, the polyunsaturated oil is a unique marine-derived oil, such as wild caught Salmon, including for example, wild caught Alaskan Salmon. Applicants' compositions are unique, in that some components of the composition are prepared via a 5 supercritical CO2 extraction process. Unlike traditional solvent-based extraction methods, supercritical CO2 extraction allows the natural products in the herbs to be obtained without leaving chemical residues behind in the preparation.

The term "supercritical extraction" as used herein refers to the technique in which hydrophobic compounds can be extracted from samples utilizing a supercritical fluid. The salvation power of a supercritical fluid is increased as the pressure and temperature are increased above their critical points, producing an effective solvent for the isolation of hydrophobic molecules. The term "supercritical extracts" or "SCE" refers to extracts prepared by supercritical extraction.

As used herein, the term "fatty acid" refers to a C6 to C26 saturated or unsaturated fatty acid that may be in free form, a monoglyceride, a diglyceride, a triglyceride, an ester or solvate thereof, combinations thereof, or a pharmaceutically acceptable salt thereof. In preferred embodiments, fatty acids in compositions of the present subject matter are generally present in the form of a triglyceride molecule, which helps facilitate absorption, storage, and utilization of fatty acids within the body. In some embodiments, fatty acids in compositions of the present subject matter are present as free fatty acids, as part of triglycerides, as salts thereof, or as combinations thereof.

"Essential Fatty Acids" (EFAs) are fats one must consume in the diet since the human body does not manufacture them. EFAs are divided into two groups: omega-6 EFAs, which include linoleic acid and its derivatives, and omega-3 EFAs, which include alpha-linolenic acid and its derivatives. Both omega-3 and omega-6 EFAs are polyunsaturated fatty acids (PUFA) What distinguishes the two types is the placement of the first double bond (relative to the methyl end of the molecule) in their hydrocarbon chains: the omega-3 EFAs have their first double 5 bond at the third carbon position, whereas the omega-6 EFAs have their first double bond at the sixth carbon position. Although all the EFAs can be found in human food sources, only linoleic and alpha-linolenic acid is considered truly essential, since the body contains enzymes with which it can synthesize all the other EFAs from these two fatty acids. And, while the above is true, the relative ability of human metabolism to form EPA and DHA is poor at best which is why supplemental fish oil is needed to increase the relative proportion of healthy omega-3 fatty acids in the diet.

Preferred omega-3 lipids include, for example, Alphalinolenic acid (ALA), Eicosapentaenoic acid (EPA). Docosahexaenoic acid (DHA). Omega-6 lipids include, and for example, Linoleic acid (LA), Arachidonic acid (AA), dihomolinoleic acid (DHGA), and gamma-linoleic acid (GLA).

TABLE I

The 'Good and Bad' effects of eicosanoids

| Good" Eicosanoids" derived from omega-3 EFAs) | "Bad" Eicosanoids" (derived from omega-6 EFAs) |
|---|---|
| Prevent blood clots caused by platelet aggregation | Promote blood clots caused by platelet aggregation |
| Cause vasodilation of blood vessels | Cause vasoconstriction of blood vessels |
| Reduce pain | Promote pain |
| Decrease cell division | Promote cell division |
| Enhance the immune system | Depress the immune system |
| Improve brain function | Depress brain function |

Ref: Fish Oil. The Natural Anti-Inflammatory. By Joseph C. Maroon, M. D. and Jeffrey Bost, PAC. Basic Health Publications, 2006.

The following is an explanation of what can be considered as the 'good', 'bad' and 'neutral' classification of fatty acids as used in analyses of the compositions of the present subject matter (WholeMega compositions) resulting in the data contained herein. Some examples are contained within WholeMega at concentrations equal to or above 30 mg/1 g capsule. The designation of "C20:1W9" is explained, for example, as a molecule (fatty acid) with 20 carbons (C20) and 1 double bond, with the initial double bond located on the 9th carbon (relative to the methyl end of the molecule) in the 'omega-9 position'. Likewise, the designation for DHA is written as C22:6W3 which stands for a molecule with 22 carbons and 6 double bonds, with the first double bond occurring at the third carbon from the end (omega position) of the molecule. This makes it an 'omega-3' fatty acid.

1. "Good" Fats:
Monounsaturated Fatty Acids (MUFA)
  C1S:IWSCIS
  C16:1W7C Palmitoleic acid
  C17:1W7
  C18:1W9C Oleic acid
  C20:1W9 Eicosenoic acid=Gadoleic acid
  C22:1W9 Docosenoic acid=Erucic acid
  C24:1W9C
  Essential Fatty Acids (EFA)
  C18:3W3 Alpha-linolenic
  C18:2W6C Linoleic
  Highly-Unsaturated Fatty Acids (HUFA)
  C20:SW3 EICOSAPENTAENOIC (EPA)
  C22:6W3 DOCOSAHEXAENOIC (DHA)

2. "Bad" Fats:
Saturated Fatty Acids
  C16:0 PALMITIC
  C17:0 HEPTADECANOIC
  C18:0 STEARIC
  C20:0 ARACHIDIC
  C21:0 HENEICOSANOIC
  C22:0 BEHENIC
  C23:0 TRICOSANOIC
  C24:0 LIGNOCERIC
  Trans-Fatty Acids (TFA)
  C18:1W9T
  C18:2W6T 3. "Neutral" Fats
Poly-unsaturated Fatty Acids (PUFA)
  C20:3W3 Eicosatrienoic acid (ETA)
  C18:3W6 GAMMA-LINOLENIC
  C20:2W6 EICOSADIENOIC
  C20:3W6 DGLA
  C20:4W6 Arachidonic acid (AA)
  C22:2W6 DDA As used herein, "subject" or "individual" or "animal" or "patient" or "mammal," refers to any subject, particularly a mammalian subject, for whom diagnosis, prognosis, or therapy is desired, for example, a human.

As used herein, a "treatment" or "treating" of a disease, disorder, or condition encompasses alleviation of at least one symptom thereof, a reduction in the severity thereof, or the delay, prevention, or inhibition of the progression thereof. Treatment need not mean that the disease, disorder, or condition is totally cured. A useful composition herein needs only to reduce the severity of a disease, disorder, or condition, reduce the severity of symptoms associated therewith, provide improvement to a patient or subject's quality of life, or delay, prevent, or inhibit the onset of a disease, disorder, or condition.

Any concentration ranges, percentage range, or ratio range recited herein are to be understood to include concentrations, percentages or ratios of any integer within that range and fractions thereof, such as one tenth and one hundredth of an integer, unless otherwise indicated.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application. For example, "a" polymer refers to both one polymer or a mixture comprising two or more polymers.

Throughout the application, descriptions of various embodiments use "comprising" language; however, it will be understood by one of skill in the art, that in some specific instances, an embodiment can alternatively be described using the language "consisting essentially of" or "consisting of."

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Other terms as used herein are meant to be defined by their well-known meanings in the art.

The Subject Compositions

The subject compositions are a genus of polyherbal and polyunsaturated oil preparations comprising constituents which exhibit anti-proliferative, anti-inflammatory, antioxidant, anti-angiogenic, and apoptotic activities. The subject therapeutic compositions are comprised of therapeutically effective amounts (A) an herbal composition and (B) a polyunsaturated oil composition.

Herbal Composition

In some embodiments, the herbal composition comprises therapeutically effective amounts of at least one herbal component selected from the group consisting of an extract of rosemary, and an extract of oregano. In one embodiment, the herbal composition comprises a supercritical extract of rosemary, a supercritical extract of oregano, or combinations thereof. Other nonlimiting extracts of rosemary and oregano may include alcohol extracts for example. In another embodiment, the herbal composition consists essentially of therapeutically effective amounts of supercritical extracts of rosemary, and supercritical extracts of oregano. The herbal composition may also comprise one or more additional components, such as a vegetable oil, a non-limiting example of a suitable vegetable oil is sunflower oil. In one embodiment, sunflower oil is added as a carrier to the rosemary supercritical extract to make the extract easier to pour and mix into solution. In one embodiment, 0.04 mg of sunflower oil is added to every 2 mg of rosemary supercritical extract.

In some embodiments, the herbal composition provides an antioxidant function and/or a formulation stability function when combined with the polyunsaturated oil composition of the present subject matter. In certain embodiments, the herbal composition inhibits the oxidation of polyunsaturated lipids and/or stabilizes the inherent chemical reactivity of polyunsaturated lipids in compositions of the present subject matter, and thereby provides for longer shelf-life and/or a more consistent chemical profile of the compositions of the present subject matter.

Commercial fish oils are usually processed with the addition of natural antioxidants, such as tocopherols. The levels of tocopherols added to such polyunsaturated oils have been thought to be generally sufficient to prevent excessive oxidation of the polyunsaturated oil. It has been unexpectedly found that an herbal oil composition of the present subject matter is useful for further inhibiting the oxidation of polyunsaturated oils beyond what is provided by the antioxidants (such as 500 ppm α-tocopherol) that are added at the time the oil is initially processed. An oxidation study was conducted and it was found that the herbal oil compositions of the present subject matter provide additional unexpectedly significant protection of polyunsaturated oils from oxidation.

Table II shows comparative oxidation polyunsaturated oil with and without an herbal the present subject matter.

TABLE II

| Sample | Sample Description | Duration of exposure (hr.) | Protection Value |
|---|---|---|---|
| 1 | Salmon oil without addition of Herbal Antioxidant Composition | 7.2 | 1.0 |
| 2 | Salmon oil without addition of Herbal Antioxidant Composition | 7.5 | 1.0 |
| 3 | Salmon oil with 0.2% Rosemary AO + 0.1% Oregano SCE | 25.7 | 3.5 |
| 4 | Salmon oil with 0.2% Rosemary AO + 0.1% Oregano SCE | 21.4 | 2.9 |

In this example, the Rancimat induction time method was employed for measuring the time required to induce a predetermined level of oxidation of composition of the present subject matter. The Metrohm 679 Rancimat equipment measured the level of oxidation and oxidative stability of samples. In this test, 4 grams of sample were placed in the instrument and air at 80° C. was flowed across the sample at 10 liters per hour. The control samples (processed salmon oil alone, containing 500 ppm of alpha-tocopherol added by the processor) were then run for 7.2 and 7.5 hours until a sufficient oxidation peak was measured on the equipment. The time to reach the measured level of oxidation was assigned a "protection value" of 1.0. Test samples were then run where the indicated extracts of rosemary and oregano oil were added to the salmon oil composition. The oxidation test was then run and it was found that it took significantly longer for the samples to reach the same level of oxidation reached by the controls at the end of 7.2 and 7.5 hours. The time to reach the same level of oxidation in the test samples were at least doubled, and specifically were increased by at least a factor of 2.9, and up to a factor of 3.5 for the test samples. Thus the "protection value" for these samples ranged from about 2.9 to about 3.5, as compared to the protection value of 1.0 for salmon oil without the herbal oil composition.

Supercritical extracts of rosemary and oregano used in the present subject matter can be prepared according to known supercritical extraction methods, such as disclosed, e.g., in E. Stahl, K. W. Quirin, D. Gerard, Dense Gases for Extraction and Refining, Springer Verlag 4 1988, which is hereby incorporated by reference herein.

In another embodiment, the herbal composition, without polyunsaturated oil, comprises:
(A) a supercritical extract of rosemary from about 5% to about 80%, and alternatively from about 50% to about 75%, by weight of the herbal composition, without polyunsaturated oil; and
(B) a supercritical extract of oregano from about 5% to about 60%, and alternatively from about 15% to about 40%, by weight of the herbal composition, without polyunsaturated oil. In a further embodiment, the herbal composition comprises a ratio of SCE rosemary:SCE oregano at a ratio of about 1:1, and more preferably at a ratio of about 2:1. In further embodiments, the herbal composition may be combined with a polyunsaturated oil composition. In one embodiment, 2 mg of SCE rosemary and 1 mg of SCE oregano are combined with 2 grams of polyunsaturated oil.

Polyunsaturated Oil Composition

In further embodiments, the marine oil or polyunsaturated oil composition comprises at least one essential fatty acid selected from the group consisting of DHA, EPA, and alphalinolenic acid. In some embodiments, the polyunsaturated oil composition is a marine oil. In a further embodiment, the polyunsaturated oil composition comprises salmon oil preferably from wild caught Alaskan salmon. In other embodiments, the polyunsaturated oil composition comprises polyunsaturated fatty acids derived from one or more oil sources selected group consisting of fish oils, seed oils, plant oils, and algaoils.

In further embodiments, the marine oil or polyunsaturated oil composition further comprises at least one non-fatty acid component, such as for example at least one non-fatty acid component naturally found in wild caught salmon. In one embodiment, at least one non-fatty acid component is a non-fatty acid lipid (such as cholesterol, etc.), a vitamin (such as vitamin D, etc.), an antioxidant (such as a tocopherol, etc), a pigment (such as astaxanthin, etc), or mixtures thereof. In one embodiment the polyunsaturated oil composition comprises a fatty acid component (such as in the form of triglycercides, diglycerides, monoglycerides, phospholipids, free fatty acids, esterified fatty acids, salts thereof, or combinations thereof), cholesterol, vitamin D, and astaxanthin.

Organic solvents, such as hexane, are sometimes used to purify or concentrate polyunsaturated oils from oil sources, such as fish or algae, and trace amounts of the solvent can then remain in the purified oil and contribute to adverse health effects. In one embodiment of the present subject matter, the polyunsaturated oil is free of organic solvent, such as hexane, and is thus free of such adverse health effects.

In a further embodiment, the polyunsaturated oil composition comprises from about 10% to about 60%, alternatively from about 15% to about 35%, and further alternatively about 20%, by weight of DHA (docosahexaenoic 30 acid).

In a composition alternatively polyunsaturated 10% to about oil 60%, further embodiment, the comprises from about from about 10% to about 35%, and further alternatively about 10%, by weight of EPA (eicosapentaenoic acid).

In a further embodiment, the polyunsaturated oil composition comprises from about 1.0% to about 2.4%, 5 alternatively from about 0.8% to about 2.2%, and further alternatively about 2%, by weight of octadecatrienoic acid.

In a further embodiment, the polyunsaturated oil composition comprises from about 0.3% to about 1.4%, alternatively from about 0.8% to about 1.2%, and further alternatively about 1%, by weight of heneicosapentaenoic acid.

In a further embodiment, the polyunsaturated oil composition comprises from about 0.03% to about 0.4%, alternatively from about 0.08% to about 0.2%, and further alternatively about 0.05%, by weight of tetradecenoic acid.

In a further embodiment, the polyunsaturated oil composition comprises from about 2.6% to about 6.4%, alternatively from about 1.8% to about 8.2%, and further alternatively about 5%, by weight of hexadecenoic acid.

In a further embodiment, the polyunsaturated oil composition comprises from about 14.0% to about 20.0%, alternatively from about 10.8% to about 20.2%, and further alternatively about 15%, by weight of octadecenoic acid.

In a further embodiment, the polyunsaturated oil composition comprises from about 4.0% to about 10.0%, alternatively from about 5.8% to about 9.2%, and further alternatively about 8%, by weight of eicosenoic acid.

In a further embodiment, the polyunsaturated oil composition comprises from about 5.0% to about 10.0%, alternatively from about 5.8% to about 8.2%, and further alternatively about 7%, by weight of docosenoic acid.

In a further embodiment, the polyunsaturated oil composition comprises from about 0.4% to about 1.4%, alternatively from about 0.8% to about 2.2%, and further alternatively about 1%, by weight of tetracosenoic acid.

It is also recognized that the preferred composition may contain minor amounts (0.01 to 3% by weight) of the following polyunsaturated oils: octadecadienoic acid, octadecatetraenoic acid, eicosatetraenoic acid, eicosadienoic acid, heptadecenoic acid and eicosatrienoic acid.

In certain embodiments, the subject compositions comprise a polyunsaturated oil composition that has a favorable ratio of good fats to bad fats. For example, the phospholipids oil composition may comprise increased concentrations of "good fats" selected from the group consisting of C15: 1W5CIS; C16:1W7C Palmi toleic acid; C17: 1W7; C18: 1W9C Oleic acid; C20: 1W9 Eicosenoic acid Gadoleic acid; C22:1W9 Docosenoic acid Erucic acid; C24:1W9C; C18: 3W3 Alpha-linolenic; C18:2W6C Linoleic; C20: 5W3 EICOSAPENTAENOIC (EPA); and C22: 6W3 DOCOSAHEXAENOIC (DHA) Also for example, the phospholipid oil composition may comprise decreased concentrations of "bad fats" selected from the group consisting of C16:0 PALMITIC; C17:0 HEPTADECANOIC; C18:0 STEARIC; C20:0 ARACHIDIC; C21:0 HENEICOSANOIC; C22:0 BEHENIC; C23:0 TRICOSANOIC; C24:0 LIGNOCERIC; C18:1W9T; and C18:2W6T.

In some embodiments, the phospholipid oil composition may also comprise "neutral fats" selected from the group consisting of C20:3W3 Eicosatrienoic acid (ETA); C18: 3W6 GAMMA-LINOLENIC; C20:2W6 EICOSADIENOIC; C20:3W6 DGLA; C20:4W6 Arachidonic acid (AA); and C22:2W6 DDA.

In some embodiments, the polyunsaturated oil composition comprises a ratio of good fats to bad fats ranging from 2:1 to 100:1, for example 5:1, 7:1, 10:1, 15:1, 20:1, 25:1, or 30:1. In at least one embodiment, there are no detectable bad fats in the polyunsaturated oil composition.

Therapeutic Compositions

In certain embodiments, the therapeutic composition of the present subject matter comprises a therapeutically effective amount of a supercritical extract of rosemary and a supercritical extract of oregano. In one embodiment, the therapeutic composition of the present subject matter consists essentially of a therapeutically effective amount of a supercritical extract of rosemary and a supercritical extract of oregano.

In other embodiments, a therapeutic composition is prepared by combining an herbal composition described herein with a polyunsaturated oil composition described herein. In another embodiment, the therapeutic composition of the present subject matter comprises a therapeutically effective amount of supercritical extract of rosemary and supercritical extract of oregano in combination with a polyunsaturated oil composition. In a further embodiment, the polyunsaturated oil composition comprises a fish oil, such as, for example, salmon oil. In one embodiment, the therapeutic composition of the present subject matter consists essentially of a therapeutically effective amount of a supercritical extract of rosemary, a supercritical extract of oregano, and fish oil, such as salmon oil.

In one embodiment, the therapeutic composition comprises an herbal composition to polyunsaturated oil composition ratio ranging from 1:5 to 1:5000, for example, 1:5, 1:10, 1:20, 1:30, 1:40, 1:50, 1:100, 1:200, 1:300, 1:500, 1:1000, 1:2000, 1:3000, 1:4000, or 1:5000.

In an alternate aspect, the therapeutic composition comprises an additional agent selected from the group consisting of antineoplastic agents, antioxidants, growth inhibiting agents, herbal extracts, and other nutrients. In certain embodiments, the therapeutic compositions of the present subject matter do not contain therapeutically effective amounts of supercritical extracts of turmeric or ginger; or therapeutically effective amounts of hydroalcoholic extracts of holy basil, ginger, turmeric, Scutellaria baicalensis, rosemary, green tea, huzhang, Chinese goldthread, or barberry; nor combinations thereof.

In some preferred embodiments, the therapeutic compositions of the present subject matter do not contain the herbal composition Zyflamend® (NewChapter, Inc., Brattleboro, Vt.)

Set forth in Table III is an exemplary embodiment of the orally administered composition, excluding inactive ingredients, as used in the methods of the present subject matter. The amounts recited in Table II represent the capsule dosage of the ingredients listed.

TABLE III

| Ingredient | Type of Extract | Source | Amount (mg) |
| --- | --- | --- | --- |
| Rosemary | supercritical | leaf | 0.5 to 4 |
| Oregano | supercritical | leaf | 0.25 to 4 |
| Salmon Oil | | Salmon | 500 to 1000 |

In some embodiments, the composition comprises 2 grams of fish oil; 2 mg of SCE rosemary; and 1 mg of SCE oregano. In one embodiment, the fish oil comprises Alaskan Salmon oil, such as extra-virgin wild Alaskan Salmon oil. In a further embodiment, the composition consists essentially of polyunsaturated oil; SCE rosemary; and SCE oregano.

In certain embodiments, the composition comprises 1000-2000 mg of fat from wild Alaskan Salmon oil, 5-20 mg cholesterol, 20-200 IU vitamin D, 2-10 micrograms astaxanthin, 1-6 mg SCE rosemary, and 1-3 mg SCE oregano. In a particular embodiment, 2000 mg of polyunsaturated oil comprises about 480 mg of saturated fat, about 840 mg of monounsaturated fat, and about 680 mg polyunsaturated fat. In a further embodiment, 2000 mg of polyunsaturated oil comprises about 500 mg of omega-3 fatty acids, about 1 mg of omega-5 fatty acids, about 140 mg of omega-6 fatty acids, about 100 mg omega-7 fatty acids, and about 660 mg omega-9 fatty acids. In yet another embodiment, 500 mg of 5 omega-3 fatty acids in the polyunsaturated oil comprises about 180 mg of EPA, about 220 mg of DHA, and about 100 mg of other omega-3 fatty acids (such as docosapentaenoic acid, linolenic acid, heneicosapentaenoic acid, etc.) In yet a further embodiment, the polyunsaturated oil has a EPA:DHA ratio ranging from 2:1 to 1:10, 2:1 to 1:5, 1:1 to 1:3, 1:1.5 to 1:3, or 1:2 to 1:2.5.

The term "WholeMega" as used herein refers to one exemplary formulation of a composition of the present subject matter which was used for various studies described in the figures and examples. WholeMega as used herein comprises 2000 mg of fat from wild Alaskan Salmon oil, 15 mg cholesterol, 100 IU vitamin D, 6 micrograms astaxanthin, 2 mg SCE rosemary, and 1 mg SCE oregano. WholeMega's 2000 mg of fat comprises about 480 mg of saturated fat, about 840 mg of monounsaturated fat, and about 680 mg polyunsaturated fat. Further, WholeMega's 2000 mg of fat includes about 500 mg of omega-3 fatty acids, about 1 mg of omega-5 fatty acids, about 140 mg of omega-6 fatty acids, about 100 mg omega-7 fatty acids, and about 660 mg omega-9 fatty acids. In addition, the 500 mg of omega-3 fatty acids in WholeMega comprises about 180 mg of EPA, about 220 mg of DHA, and about 100 mg of other omega-3 fatty acids (such as docosapentaenoic acid, linolenic acid, heneicosapentaenoic acid, etc.) Additional non-limiting examples of the WholeMega formulation are contemplated, and subsequent compositions labeled as "WholeMega" may have variations in the formulation described above and subsequent variations will be described in updated product labeling as needed.

Methods of the Present Subject Matter

The compositions of the present subject matter generally comprise standardized supercritical $CO_2$ concentrated extracts of rosemary and oregano, and optionally a polyunsaturated oil composition.

The subject compositions were investigated for their ability to incorporate polyunsaturated lipids into tissue membranes where they serve to modulate cell signal events (e.g. reduce inflammation) and increase membrane fluidity. The change in serum lipid content after administration of the subject compositions results in an increase in heal thy omega-3 oils, such as EPA, and a relative fall in the omega-6 oil arachidonic acid (AA). This change has been shown to be dose dependent and can be considered as beneficial and reduces the inflammatory potential.

In some embodiments, therapeutically effective doses of the compositions of the present subject matter are useful for treating cardiovascular disease resulting from the buildup of arterial plaque from oxidized low density lipoprotein. In addition, in further embodiments, therapeutically effective doses of the compositions of the present subject matter promote the presence of high density lipoprotein (HDL) in the body and is understood to have beneficial health effects. For example, HDL is known to be a more soluble form of lipoprotein, hence its presence does not significantly contribute to the formation of arterial plaque. In addition, it is known that HDL is able to absorb plaque material and may thus directly reduce the amount of arterial plaque.

In one embodiment, compositions of the present subject matter are effective for reducing platelet aggregation and serum triglycerides which may reduce the risk of myocardial infarction, hypertension, atherosclerosis, and certain types of cancer. In another embodiment, compositions of the present subject matter are effective for promoting eicosanoid synthesis and modulation beneficial for health.

In one embodiment, compositions of the present subject matter are effective for treating glycogen storage disease, vascular disease, stroke, diabetes, rheumatoid arthritis, spinal pain, osteoarthritis, inflammatory bowel disease, systemic lupus erythematosis, multiple sclerosis, asthma, macular degeneration, eczema, psoriasis, postpartum depression, menstrual pain, Alzheimer's disease, Parkinson's disease, depression, bipolar disorder, schizophrenia, hyperlipoproteinemia, or hypercholesterolemia.

In yet other embodiments, compositions of the present subject matter are effective for preventing, treating or reducing the risk of hyperproliferative disorders, cancer, leukemia, and lymphoma.

Additional methods for using compositions of the present subject matter include promoting the beneficial health effects may be associated with supplementation of specific unsaturated lipids. Some embodiments of the present subject matter may include the following examples of unsaturated lipids and thereby promote their beneficial health effects. Table IV provides an example of the unsaturated fatty acid composition of salmon oil in some embodiments of the present subject matter. In some embodiments, marine oil or polyunsaturated oil compositions of the present subject matter may comprise one or more of the lipids listed in Table IV, and combinations thereof.

Table IV

Attorney Ref. 30188U acid C21:5 Heneicosapentaenoic 0.5 acid C22:6 Docosahexaenoic DHA 10.0 acid Omega-5 Fatty acid C14:1 Tetradecenoic acid 0.1 Omega-6 fatty acids C18:2 Octadecadienoic Linoleic acid 1.8 acid C18:4 Octadecatetraenoic Alpha-parinaric 2.4 acid C29:4 Eicosatetraenoic Arachidonic acid 1.6 acid C20:2 Eicosadienoic acid 0.4 Omega-7 fatty acid C16:1 Hexadecenoic acid Palmitoleic acid 4.9 Omega-9 fatty acids C15:1 Pentadecenoic acid 0.1 C17:1 Heptadecenoic acid Margaroleic acid 0.4 C18:1 Octadecenoic acid Oleic acid 14.2 C20:1 Eicosenoic acid Gadoleic acid 8.4 C20:3 Eicosatrienoic acid 0.3 C22:1 Docosenoic acid Eurcic acid 8.7 C24:1 Tetracosenoic acid Nervonic acid 0.8 The present subject matter also provides for a process of making a combined herbal and polyunsaturated oil composition, comprising combining one of the herbal compositions described herein with one of the polyunsaturated oil compositions.

TABLE IV

| Omega-3 fatty acids | | Common name | Average % by weight of oil composition |
|---|---|---|---|
| C18:3 | Octadecatrienoic acid | Alpha-linoleic acid | 1.6 |
| C20:5 | Eicosapentaenoic | EPA | 9.0 |
| C21:5 | Heneicosapentaenoic acid | | 0.5 |
| C22:6 | Docosahexaenoic acid Omega-5 Fatty acid | DHA | 10.0 |
| C14:1 | Tetradecenoic acid Omega-6 fatty acids | | 0.1 |
| C18:2 | Octadecadienoic acid | Linoleic acid | 1.8 |
| C18:4 | Octadecatetraenoic acid | Alpha-parinaric acid | 2.4 |
| C29:4 | Eicosatetraenoic acid | Arachidonic acid | 1.6 |
| C20:2 | Eicosadienoic acid Omega-7 fatty acid | | 0.4 |
| C16:1 | Hexadecenoic acid Omega-9 fatty acids | Palmitoleic acid | 4.9 |
| C15:1 | Pentadecenoic acid | | 0.1 |
| C17:1 | Heptadecenoic acid | Margaroleic acid | 0.4 |
| C18:1 | Octadecenoic acid | Oleic acid | 14.2 |
| C20:1 | Eicosenoic acid | Gadoleic acid | 8.4 |
| C20:3 | Eicosatrienoic acid | | 0.3 |
| C22:1 | Docosenoic acid | Eurcic acid | 8.7 |
| C24:1 | Tetracosenoic acid | Nervonic acid | 0.8 |

The present subject matter also provides for a process of making a combined herbal and polyunsaturated oil composition, comprising combining one of the herbal compositions described herein with one of the polyunsaturated oil compositions described herein. In one embodiment of the process, the herbal oil comprises 2 mg SCE rosemary and 1 mg SCE oregano and the polyunsaturated oil comprises 2000 mg of fish oil, such as wild caught Alaskan Salmon oil, and the herbal oil and polyunsaturated oil are combined together and optional prepared in a dosage form, such as a capsule.

1. EPA and DHA

Much is known about the health benefits of increasing intake of omega-3 fatty acids such as EPA and DHA relative to omega-6 (e.g. arachidonic acid) intake. For example, see Dr. Joseph C. Maroon's 2006 book titled: "Fish Oil. The Natural Anti-Inflammatory".

2. Oleic Acid

Oleic acid is the major monounsaturated fatty acid in the body. An animal's diet provides the body's main source of oleic acid, however, it can also be synthesized in limited amounts from stearic acid via the action of the delta-9-desaturase enzyme. The most notable dietary source is olive oil, which consists of 70-80%% oleic acid. Other good sources include: grape seed oil, sea buckthorn oil, and the pulp of the Brazilian palmberry, acai. Numerous studies indicate that a diet rich in olive oil decreases the development of atherosclerosis and lowers serum cholesterol by diminishing oxidative stress and inflammatory mediators. While the health benefits of olive oil are frequently attributed to the phenolic compounds present, a recent study suggests that the oleic acid itself is responsible for its blood pressure lowering effects. Additionally, oleic acid displays anti-tumor activity. It was shown to not only block the action of a cancer-causing oncogene called HER-2/neu which is present in about 30 percent of breast cancer patients, but also improve the effectiveness of the breast cancer drug Herceptin.

Oleic acid is an ingredient in Lorenzo's oil an experimental treatment for a rare neurobiology disorder called adrenoleukodystrophy. Proc Natl Acad Sci USA. 2008 Sep. 16; 105(37):13811-6. Epub 2008 Sep. 4. Oleic acid content is responsible for the reduction in blood pressure induced by olive oil. Teres S, Barceló-Coblijn G, Benet M, Alvarez R, Bressani R, Halver J E, Escrib§PV. Laboratory of Molecular Cell Biomedicine, 5 Department of Biology, Institut Universitari d'Investigacions en Ciencies de la Salut, University of the Balearic Islands, Carretera de Valldemossa Km 7.5, E-07122 Palma de Mallorca, Spain.

Numerous studies have shown that high olive oil intake reduces blood pressure (BP). These positive effects of olive oil have frequently been ascribed to its minor components, such as alpha-tocopherol, polyphenols, and other phenolic compounds that are not present in other oils. However, it has recently been demonstrated that the hypotensive effect of olive oil is caused by its high oleic acid (OA) content (approximately 70-80%). It has been proposed that olive oil intake increases OA levels in membranes, which regulates membrane lipid structure (H(II) phase propensity) in such a way as to control G protein-mediated signaling, causing a reduction in BP. This effect is in part caused by its regulatory action on G protein-associated cascades that regulate adenylyl cyclase and phospholipase C. In turn, the OA analogues, elaidic and stearic acids, had no hypotensive activity, indicating that the molecular mechanisms that link membrane lipid structure and BP regulation are very specific. Similarly, soybean oil (with low OA content) did not reduce BP. It has been demonstrated that olive oil induces its hypotensive effects through the action of ~A.

Ann Oncol. 2005 March; 16(3):359-71. Epub 2005 Jan. 10. Oleic acid, the main monounsaturated fatty acid of olive oil, suppresses Her-2/neu (erbB-2) expression and synergistically enhances the growth inhibitory effects of trastuzumab (Herceptin) in breast cancer cells with Her-2/neu oncogene amplification. Menendez J A, Vellon L, Colomer R, Lupu R. Department of Medicine, Breast Cancer Translational Research Laboratory, Evanston Northwestern Healthcare Research Institute, 1001 University Place, Evanston, Ill. 60201, USA.

The relationship between the intake of olive oil, the richest dietary source of the monounsaturated fatty acid oleic acid (OA; 18: In-9), and breast cancer risk and progression has become a controversial issue. Moreover, it has been suggested that the protective effects of olive oil against breast cancer may be due to some other components of the oil rather than to a direct effect of ~A.

Methods:

Using flow cytometry, western blotting, immunofluorescence microscopy, metabolic status (MTT), soft-agar colony formation, enzymatic in situ labeling of apoptosis-induced DNA double-strand breaks (TUNEL assay analyses), and caspase-3-dependent poly-ADP ribose polymerase (PARP) cleavage assays, the effects of exogenous supplementation with OA on the expression of Her-2/neu oncogene were demonstrated. The expression of Her-2/neu oncogene plays an active role in breast cancer etiology and progression. In addition, the effects of OA on the efficacy of trastuzumab (Herceptin), a humanized monoclonal antibody binding with high affinity to the ectodomain of the Her-2/neu-coded p18S(Her-2/neu) oncoprotein were investigated. To study these issues BT-474 and SKBr-3 breast cancer cells were used, which naturally exhibit amplification of the Her-2/neu oncogene.

Results:

Flow cytometric analyses demonstrated a dramatic (up to 46%) reduction of cell surface-associated p18S (Her-2/neu) following treatment of the Her-2/neu-overexpressors BT-4 7 4 and 30 SK-Br$_3$ with ~A. Indeed, this effect was comparable to that found following exposure to optimal concentrations of trastuzumab (up to 48% reduction with 20 microg/ml trastuzumab). Remarkably, the concurrent exposure to OA and suboptimal concentrations of trastuzumab (5 microg/ml) synergistically down-regulated Her-2/neu expression, as determined by flow cytometry (up to 70% reduction), immunoblotting, and immunofluorescence microscopy studies. The nature of the cytotoxic interaction between OA and trastuzumab revealed a strong synergism, as assessed by MTT based cell viability and anchorage-independent soft-agar colony formation assays. Moreover, OA co-exposure synergistically enhanced trastuzumab efficacy towards Her-2/neu overexpressors by promoting DNA fragmentation associated with apoptotic cell death, as confirmed by TUNEL and caspase-3-dependent PARP cleavage. In addition, treatment with OA and trastuzumab dramatically increased both the expression and the nuclear accumulation of p27 (Kip1), a cyclin-dependent kinase inhibitor playing a key role in the onset and progression of Her-2/neu-related breast cancer. Finally, OA co-exposure significantly enhanced the ability of trastuzumab to inhibit signaling pathways downstream of Her-2/neu, including phosphoproteins such as AKT and MAPK.

Conclusions:

These findings demonstrate that OA, the main monounsaturated fatty acid of olive oil, suppresses Her-2/neu overexpression, which, in turn, interacts synergistically with anti-Her-2/neu immunotherapy by promoting apoptotic cell death of breast cancer cells with Her-2/neu oncogene amplification. This previously unrecognized property of OA offers a novel molecular mechanism by which individual fatty acids, and compositions of the present subject matter, may regulate the malignant behavior of breast cancer cells and therefore be helpful in the design of future epidemiological studies and, eventually, dietary counseling.

Am J Clin Nutr. 1998 July; 68 (1):134-41. Tissue stores individual monounsaturated fatty acids and breast cancer: the EURAMIC study. European Community Multicenter Study on Antioxidants, Myocardial Infarction, and Breast Cancer. Simonsen N R, Fernandez-Crehuet Navaj as J, Martin-Moreno J M, Strain J J, Huttunen J K, Martin B C, Thamm M, Kardinaal A F, Veer P, Kok F J, Kohlmeier L. University of North Carolina, Chapel Hill, 27599, USA.

The strongest evidence that monunsaturated fat may influence breast cancer risk comes from studies of southern European populations, in whom intake of oleic acid sources, particularly olive oil, appears protective. No previous study has examined the relation of adipose tissue fatty acid content to breast cancer in such a population. Adipose biopsies with diverse fat intake patterns gathered in 5 European centers, including southern Europe (Malaga, Spain) were used to test the hypothesis that stores of oleic acid or other monounsaturates are inversely associated with breast cancer. Gluteal fat aspirates were obtained from 291 postmenopausal incident breast cancer patients and 351 control subjects, frequency-matched for age and catchment area. Logistic regression was used to model breast cancer by monounsaturates, with established risk factors controlled for. Oleic acid showed a strong inverse association with breast cancer in the Spanish center. The odds ratio for the difference between 75th and 25th percentiles was 0.40 (95% CI: 0.28, 0.58) in Malaga and 1.27 (0.88, 1.85) in all other centers pooled, with a peak at 2.36 (1.01, 5.50) for Zeist. Palmitoleic and myristoleic acids showed evidence of an inverse association outside Spain, and cis-vaccenic acid showed a positive association in 3 centers. These data do not support the hypothesis that increasing tissue stores of oleic acid are protective against breast cancer in non-Spanish populations. This finding implies that the strong protective associations reported for olive oil intake in dietary studies may be due to some other protective components of the oil and not to the direct effect of oleic acid uptake. Alternatively, high olive oil intake may indicate some other protective aspect of the lifestyle of these women.

3. Erucic Acid

Erucic acid is monounsaturated fatty acid common to the seeds of flowering plants in the Bras sicaceae family including 5 rapeseed, wallflower seed, and mustard seed . . . all of which contain 40-50% erucic acid. Normally, erucic acid is not found or occurs in traces in body fat, but when the diet contains rapeseed oil, erucic acid is found in depot fat, organ fat and milk fat.

A four-to-one mixture of erucic acid and oleic acid constitutes Lorenzo's oil: an experimental treatment for a rare neurobiology disorder adrenoleukodystrophy. While no negative health effects have ever been documented in humans, erucic acid is not generally seen as a favorable fatty acid as long term consumption of high erucic acid rapeseed oil in rats was shown to cause heart lesions and growth retardation. Scientists have since pointed out that rats do not metabolize fats the same way as humans, so they do not provide a good model for understanding the effects of erucic acid in humans. Regardless, in 1991 the European Union banned foods containing high amounts of erucic acid. Canola oil is marketed as a low erucic acid version of rapeseed. Can J Comp Med. 1975 July; 39(3):261-9. Cardiac lesions in rats fed rapeseed oils. Charlton K M, Corner A H, Davey K, Kramer J K, Mahadevan S, Sauer F D.

Fully refined rapeseed oils containing different amounts of erucic acid (1.6%, 4.3% and 22.3%) were fed, at 20% by weight of diet, to weanling male and female Sprague-Dawley rats for periods up to 112 days. Transient myocardial lipidosis characterized by accumulation of fat droplets in myocardial fibers was marked in male and female rats fed oxidized and unoxidized rapeseed oil containing 22.3% erucic acid, moderate with rapeseed oil containing 4.3% erucic acid and very slight in rats fed rapeseed oil containing 1.6% erucic acid. Peak intensity of myocardial lipidosis occurred at three to seven days and regressed thereafter. Focal myocardial necrosis and fibrosis occurred in male rats fed rapeseed oils containing different levels of erucic acid for 112 days. The incidence of myocardial necrosis and fibrosis was markedly lower in female rats, and the incidence of these lesions in either sex was not affected by the state of oxidation of these oils. In a second experiment, male rats were fed diets containing crude, partially refined or fully refined rapeseed oils. There was no correlation between the number of foci of myocardial necrosis and fibrosis and the state of refinement of the oils, but there were generally fewer lesions in rats fed those oils having the lowest levels of erucic acid.

Acta Med Scand Suppl. 1975; 585:5-13. Physiopathological effects of rapeseed oil: a review. Borg K. Rapeseed oil has a growth retarding effect in animals. Some investigators claim that the high content of erucic acid in rapeseed oil alone causes this effect, while others consider the low ratio saturated/monounsaturated fatty acids in rapeseed oil to be a contributory factor. Normally erucic acid is not found or occurs in traces in body fat, but when the diet contains rapeseed oil erucic acid is found in depot fat, organ fat and milk fat. Erucic acid is metabolized in vivo to oleic acid. The effects of rapeseed oil on reproduction and adrenals, testes, ovaries, liver, spleen, kidneys, blood, heart and skeletal muscles have been investigated. Fatty infiltration in the heart muscle cells has been observed in the species investigated. In long-term experiments in rats erucic acid produces fibrosis of the myocardium. Erucic acid lowers the respiratory capacity of the heart mitochondria. The reduction of respiratory capacity is roughly proportional to the content of erucic acid in the diet, and diminishes on continued administration of erucic acid. The lifespan of rats is the same on corn oil, soybean oil, coconut oil, whale oil and rapeseed oil diet. Rats fed a diet with erucic acid or other docosenoic acids showed a lowered tolerance to cold stress (+4 degrees C.). In Sweden erucic acid constituted 3-4% of the average intake of calories up to 1970 compared with about 0.4% at present.

4. Gadoleic Acid

Gadoleic acid is a cis-unsaturated fatty acid present in vegetable oils and fish oil. According to Dr. Jim Duke, there are no biological activities recorded for it.

5. Palmitoleic Acid

Palmitoleic acid is a minor monounsaturated omega fatty acid in the human diet and in the blood. Dietary sources include animal fats, particularly from fish, as well as *macadamia* nuts and sea buckthorn berry. It can be produced in the body from palmitic acid, the most common saturated fatty acid in the diet, via the enzymatic action of delta-9-desaturase. Palmi toleic acid is a common constituent of the triglycerides that make up human adipose tissue. Because of this, serum levels are considered to be an independent marker of triglyceridemia and abdominal obesity.

Palmitoleic acid seems to play an important role in regulating fat and blood sugar metabolism in the adipose tissue and in the pancreas. It was shown to function as a lipokine (hormone) in mice muscle which strongly stimulates insulin action and suppresses epatosteatosis. Adipose tissues use lipokines to communicate with distant organs and regulate systemic metabolic homeostasis. Additionally, palmitoleic acid may be important for maintaining the health of insulin producing beta cells in the pancreas. In vitro studies have shown that it can counteract the cytotoxic effects of palmitic acid on beta cells as well as improve beta-cell function.

Palmitoleic acid is a major fatty acid in the cell membranes of epithelial cells such as those that make up the skin, blood vessels, and mucous membranes, where it is believed to play a protective role. Of all the fatty acids present in 5 human sebum, palmitoleic acid was shown to have the strongest antimicrobial action against gram positive bacteria. The same study showed that palmitoleic acid blocked the adherence of a pathogenic strain of *Candida albicans* to porcine stratum corneum.

Although palmitoleic acid has been accused of behaving like a saturated fat in LDL cholesterol, a recent animal study concluded that palmitoleic acid does not adversely affect plasma lipoprotein profiles or aortic cholesterol accumulation and behaves similar to other unsaturated fatty acid-rich oils. Clin Exp Pharmacol Physiol. 2004 December; 31 Suppl 2: S37-8. Serum lipid effects of a monounsaturated (palmitoleic) fatty acid-rich diet based on *macadamia* nuts in healthy, young Japanese women. Hiraoka-Yamamoto J, Ikeda K, Negishi H, Mori M, Hirose A, Sawada S, Onobayashi Y, Kitamori K, Kitano S, Tashiro M, Miki T, Yamori Y. Frontier Health Science, Mukogawa Women's University, Nishinomiya, Japan. junko@mwu.mukogawa-u.ac.jp Recent studies have identified potential beneficial effects of eating nuts, most of which have substantial amounts of monounsaturated fatty acids (MUFA). *Macadamia* nuts consist of 75% fat by weight, 80% of which is MUFA (palmitoleic acid). 2. To examine variations in serum lipid levels in response to a high-MUFA diet based on *macadamia* nuts, 3 week interventions of *macadamia* nuts, coconuts and butter were determined in young, healthy Japanese female students. 3. After 3 weeks intervention, serum concentrations of total cholesterol and low-density lipoprotein-cholesterol were significantly decreased in the *macadamia* nut and coconut diets and bodyweight and body mass index were decreased in the group fed *macadamia* nuts, although there were no statistically significant changes in the group fed butter.

J Nutr. 2009 February; 139(2):215-21. Epub 2008 Dec. 23. Effects of dietary palmitoleic acid on plasma lipoprotein profile and 5 aortic cholesterol accumulation are similar to those of other unsaturated fatty acids in the FIB golden Syrian hamster. Matthan N R, Dillard A, Lecker J L, Ip B, Lichtenstein A H. Cardiovascular Nutrition Laboratory, Jean Mayer USDA Human Nutrition Research Center on Aging at Tufts University, Boston, Mass. 02111, USA.

The lower susceptibility of palmitoleic acid (16:1) to oxidation compared to PUFA may confer functional advantages with respect to finding acceptable alternatives to partially hydrogenated fats, but limited data are available on its effect on cardiovascular risk factors. This study investigated the effect of diets (10% fat, 0.1% cholesterol, wt:wt) enriched with *macadamia* [monounsaturated fatty acid (MUFA) 16:1], palm (SFA, 16:0), canola (MUFA, 18:1), or safflower (PUFA, 18:2) oils on lipoprotein profiles and aortic cholesterol accumulation in FIB Golden Syrian hamsters (n=16/group). After 12 wk, 8 hamsters in each group were killed (phase 1). The remaining hamsters fed palm oil were changed to a diet containing coconut oil, while hamsters in the other diet groups continued on their original diets for an additional 6 wk (phase 2). With minor exceptions, the time course and dietary SFA source did not alter the study outcomes. *Macadamia* oil-fed hamsters had lower non-HDL cholesterol and triglyceride concentrations compared with the palm and coconut oil-fed hamsters and higher HDL-cholesterol compared with the coconut, canola, and safflower oil-fed hamsters. The aortic cholesterol concentration was not affected by dietary fat type. The hepatic cholesterol concentration was higher in the unsaturated compared with the saturated oil-fed hamsters. RBC membrane and aortic cholesterol ester, triglyceride, and phospholipid fatty acid profiles reflected that of the dietary oil. These data suggest that an oil relatively high in palmitoleic acid does not adversely affect plasma lipoprotein profiles or aortic cholesterol accumulation and was similar to other unsaturated fatty acid-rich oils.

Apoptosis. 2006 July; 11 (7): 1231-8. Differential protective effects of palmitoleic acid and cAMP on caspase activation and cell viability in pancreatic beta-cells exposed to palmitate. 10 Welters H J, Diakogiannaki E, Mordue J M, Tadayyon M, Smith S A, Morgan N G. Institute of Biomedical and Clinical Science, Peninsula Medical School, Devon, Research Way, Plymouth, PL6 8BU, UK.

Saturated and mono-unsaturated fatty acids exert differential effects on pancreatic beta-cell viability during chronic exposure. Long chain saturated molecules (e.g. palmitate) are cytotoxic to beta-cells and this is associated with caspase activation and induction of apoptosis. By contrast, mono-unsaturated fatty acids (e.g. palmitoleate) are not toxic and can protect against the detrimental effects of palmitate. In the present study, we show that the protective actions of palmitoleate in BRIN-BD11 beta-cells result in attenuated caspase activation following exposure to palmitate and that a similar response occurs in cells having elevated levels of cAMP. However, unlike palmitoleate, elevation of cAMP was unable to prevent the cytotoxic actions of palmitate since it caused a diversion of the pathway of cell death from apoptosis to necrosis. Palmitoleate did not alter cAMP levels in BRIN-BD11 cells and the results suggest that a change in cAMP is not involved in mediating the protective effects of this fatty acid. Moreover, they reveal that attenuated caspase activation does not always correlate with altered cell viability in cultured beta-cells and suggest that mono-unsaturated fatty acids control cell viability by regulating a different step in the apoptotic pathway from that influenced by cAMP.

Diabetes. 2001 January; 50 (1): 69-76. Distinct effects of saturated and monounsaturated fatty acids on beta-cell turnover 5 and function. Maedler K, Spinas G A, Dyntar D, Moritz W, Kaiser N, Donath M Y. Division of Endocrinology and Diabetes, University Hospital, Zurich, Switzerland.

Glucotoxicity and lipotoxicity contribute to the impaired beta-cell function observed in type 2 diabetes. Here we examine the effect of saturated and unsaturated fatty acids at different glucose concentrations on beta-cell proliferation and apoptosis. Adult rat pancreatic islets were cultured onto plates coated with extracellular matrix derived from bovine corneal endothelial cells. Exposure of islets to saturated fatty acid (0.5 mmol/l palmitic acid) in medium containing 5.5, 11.1, or 33.3 mmol/l glucose for 4 days resulted in a five- to ninefold increase of beta-cell DNA fragmentation. In contrast, monounsaturated palmitoleic acid alone (0.5 mmol/l) or in combination with palmitic acid (0.25 or 0.5 mmol/l each) did not affect DNA fragmentation. Increasing concentrations of glucose promoted beta-cell proliferation that was dramatically reduced by palmitic acid. Palmitoleic acid enhanced the proliferation activity in medium containing 5.5 mmol/l glucose but had no additional effect at higher glucose concentrations (11.1 and 33.3 mmol/l). The cell-permeable ceramide analog C2-ceramide mimicked both the palmitic acid-induced beta-cell apoptosis and decrease in proliferation. Moreover, the ceramide synthetase inhibitor fumonisin B1 blocked the deleterious effects of palmitic acid on beta-cell viability. Additionally, palmitic acid but not palmitoleic acid decreased the expression of the mitochondrial adenine nucleotide trans locator and induced release of cytochrome c from the mitochondria into the cytosol. Finally, palmitoleic acid improved beta-cell-secretory function that was reduced by palmitic acid. Taken together, these results suggest that the lipotoxic effect of the saturated palmitic acid involves an increased apoptosis rate coupled with reduced proliferation capacity of beta-cells and impaired insulin secretion. The deleterious effect of palmitate on beta-cell turnover is mediated via formation of ceramide and activation of the apoptotic mitochondrial pathway. In contrast, the monounsaturated palmitoleic acid does not affect beta-cell apoptosis, yet it promotes beta-cell proliferation at low glucose concentrations, counteracting the negative effects of palmitic acid as well as improving beta-cell function.

Skin Pharmacol Appl Skin Physiol. 2003 May-June; 16(3):176-87. Palmitoleic acid isomer (C16:1delta6) in human skin sebum is effective against gram-positive bacteria. Wille J J, Kydonieus A. ConvaTec, Bristol-Myers Squibb Co., Princeton, N.J., USA.

The percent lipid composition of pooled human sebum analyzed by thin-layer chromatography was: ceramides (13%), fatty acid (47%), cholesterol (7%), cholesterol esters (2%), squalene (11%), triglycerides (3%), and wax esters (17%) Total sebum lipids (2-4 mg/ml), sonicated into bacterial culture medium, caused 4- to 5-fold log reduction in growth of grampositive bacteria, *Staphylococcus aureus, Streptococcus salivarius* and the anaerobe *Fusobacterium nucleatum*, but was ineffective against most gram-negative bacteria. Fractionation of the sebum lipids showed that both saturated and unsaturated fatty acids contained the bulk of the antimicrobial activity. Lauric acid (C12:0) was the most active saturated fatty acid. The unsaturated fatty acid, palmitoleic acid (C16:1delta6, cPA) was both the most predominant monoene and the most active antimicrobial fatty acid. Purified cPA (>99%) yielded typical minimal inhibitory concentration (MIC) values of 10-20 microg/ml against gram-positive bacteria. Organically synthesized cPA isomer gave MIC values comparable to the natural material. Both natural and synthetic cPA were found to be the most active sebum lipid fraction in blocking the adherence of a pathogenic strain of *Candida albicans* to porcine stratum corneum. Ethanol in combination with cPA exerts a synergistic bactericidal activity against gram-negative pathogenic bacteria, including *Pseudomonas aeruginosa, Propionibacterium acnes, Escherichia coli,* and several methacillin-resistant strains of *S. aureus.* Palmitoleic acid may be useful in topical formulations for treatment of secondary gram-positive bacterial infections, as a gram-positive bacteria antimicrobial in wound dressings, and as a natural gram-positive antimicrobial products. Copyright 2003 Leukot Essent Fatty Acids. Relationships between preservative in skin and hair care S. Karger A G, Basel Prostaglandins 2006 February; 74(2):149-56. Epub 2005 December fatty acids and psychophysiological parameters in depressive inpatients under experimentally induced stress. Irmisch G, Schlafke D, Richter J. Department of Psychiatry and Psychotherapy, Rostock University, Gehlsheimer Str. 20, D-18147, Rostock, Germany.

Fatty acids can influence important cellular and hormonal processes in the human body. Non-adequate contents of fatty acids, e.g., in blood, can cause and/or result in various diseases. In depressive patients, changes in fatty acid concentrations were found (deficits in omega3-fatty acids, in particular). This paper poses the question whether there are any relations between psychophysiological parameters and changes in fatty acid compositions. The concentration of fatty acids in serum of 118 psychiatric inpatients measured directly before and after experimentally induced stress of about 1 h were analyzed in relation to psychophysiological parameters continuously registered during the experimental sessions at admission, discharge and at 3 months follow-up. Systolic and diastolic blood pressure, finger pulse amplitude, forehead temperature (FD) and the EMG activity of the musculus zygomaticus consistently correlated with concentrations of single unsaturated oleic (18:1n-9) and erucic acid (22:1) and saturated myristic (14:0) and lauric acid (12:0). Negative relations were found between FD and the concentration of arachidonic acid 5 (20:4n-6) as well as of palmitoleic acid (16:1). Furthermore, the higher the concentration of the erucic acid at discharge the higher the depression score as assessed by the Beck depression inventory (BDI). High concentrations of palmitoleic acid and lauric acid were related to a low level of depression (BDI and Hamilton scores). The implications of these findings for add-on treatment regimens in depression are discussed.

Cell. 2008 Sep. 19; 134 (6): 933-44. Identification of a lipokine, a lipid hormone linking adipose tissue to systemic metabolism. Cao H, Gerhold K, Mayers J R, Wiest M M, Watkins S M, Hotamisligil G S. Department of Genetics and Complex Diseases, Harvard School of Public Health, Boston, Mass. 02115, USA.

Dysregulation of lipid metabolism in individual tissues leads to systemic disruption of insulin action and glucose metabolism. Utilizing quantitative lipidomic analyses and mice deficient in adipose tissue lipid chaperones aP2 and mall, we explored how metabolic alterations in adipose tissue are linked to whole-body metabolism through lipid signals. A robust increase in de novo lipogenesis rendered the adipose tissue of these mice resistant to the deleterious effects of dietary lipid exposure. Systemic lipid profiling also led to identification of C16:1n7-palmitoleate as an adipose tissue-derived lipid hormone that strongly stimulates muscle insulin action and suppresses hepatosteatosis. Our data reveal a lipid-mediated endocrine network and demonstrate that adipose tissue uses lipokines such as C16:1n7-palmitoleate to communicate with distant organs and regulate systemic metabolic homeostasis.

6. Myristoleic Acid

Myristoleic acid, or 9-tetradecenoic acid, is an omega-5 fatty acid biosynthesized from myristic acid by the enzyme delta-9 desaturase. It is uncommon in nature and has undetermined biological significance in humans. One of the major sources of this fatty acid is the seed oil from plants of the genus *Myristicaceae*, a family of flowering plants sometimes called the "nutmeg family", after its most famous member, nutmeg.

Myristoleic acid can comprise up to 30 percent of the oil in some species. Myristoleic acid is also a natural component of the fat of marine animals, beavers and bovines. Myristoleic acid extracted from saw palmetto has been shown to induce apoptosis and necrosis in human prostate cancer LNCaP cells. Furthermore, myristoleic acid found in the by-products of making cheese is one of three fatty acids that are most active at inhibiting *Candida albicans* germination. Finally, myristoleic acid has been shown to inhibit the growth of *Selenomonas artemidis*, a bacteria found in high amounts in patients with periodontal disease.

Prostate. 2001 April; 47 (1):59-65. Myristoleic acid, a cytotoxic component in the extract from *Serenoa repens*, induces apoptosis and necrosis in human prostatic LNCaP cells. Iguchi K, Okumura N, Usui S, Sajiki H, Hirota K, Hirano K. Laboratory of Pharmaceutics, Gifu Pharmaceutical University, Gifu, Japan.

Background:

Prostatic tumors are well known to progress to hormonal therapy-resistant terminal states. At this stage, there are no chemotherapeutic agents to affect clinical outcome. An effective cell death inducer for these prostate cells may be a candidate as an attractive anti tumor agent. The extracts from *S. repens* have been used to improve the state of prostatic diseases and we have attempted to identify the effective component from the extract.

Methods:

Cell viability was examined in LNCaP cells, an in vitro model for hormonal therapy-resistant prostatic tumor.

Results:

It was discovered that exposure of the extract from *S. repens* resulted in cell death of LNCaP cells. Myristoleic acid was also identified as one of the cytotoxic components in the extract. The cell death exhibited both apoptotic and necrotic nuclear morphology as determined by Hoechst 33342 staining. Cell death was also partially associated with caspase activation.

Conclusions:

It was demonstrated that the extract from *S. repens* and myristoleic acid induces mixed cell death of apoptosis and necrosis in LNCaP cells. These results suggest that the extract and myristoleic acid may develop attractive new tools for the treatment of prostate cancer. FEMS Yeast Res. 2007 March; 7 (2):276-85. Epub 2006 Oct. 10. Whey-derived free fatty acids suppress the germination of *Candida albicans* in vitro. Clement M, Tremblay J, Lange M, Thibodeau J, Belhumeur P. Department de Microbiologic et Immunologic, Universite de Montreal, C. P. 6128, succ. Centreville, Montreal, QC, Canada.

Bovine whey from the cheese-making industry contains several bioactive factors that promote health and prevent disease. Although many efforts have been made over the years to show that immunoglobulins, lactoperoxidase, lactoferrin, lysosyme and small peptides present in whey have antimicrobial activities against several pathogenic microorganisms, such activities have not been investigated so far for the lipid fraction of whey. Here, we have used an in vitro assay-based fractionation procedure to show that free fatty acids derived from whey cream specifically inhibit the germination of *Candida albicans*, a morphologic change associated with pathogenicity. Further fractionation by HPLC demonstrated that this activity can be mainly attributed to lauric acid, myristoleic acid, 5 linoleic acid and arachidonic acid.

Oral Microbiol Immunol. inhibitory action of fatty acids Institut fur orale Mikrobiologie 1996 October; 11 (5): 350-5. The on oral bacteria. S. und allgemeine Shapiro Immunologic, Zentrum fur Zahn-, Mund- und Kieferheilkunde, Universitat Zurich, Switzerland.

Saturated and unsaturated fatty acids and fatty acid derivatives were examined for their growth-inhibitory effects towards three selected oral bacteria: *Porphyromonas gingivalis, Selenomonas artemidis*, and *Streptococcus sobrinus*. Of the 45 compounds surveyed, only one, myristoleic acid, was inhibitory towards *S. artemidis* at a concentration <100 micrograms/ml. cis-Hexadecenoic and cis-octadecenoic acids were generally inhibitory towards *P. gingivalis* and *S. sobrinus*, but there was no correlation between the position of the double bond and the minimum inhibitory concentration. Supra-minimum inhibitory concentrations of palmitoleic acid did not promote leakage of intracellular materials from either *P. gingi valis* or *S. sobrinus*, nor was L-isoleucine uptake by *S. sobrinus* inhibited. Fatty acids and derivatives were also examined for prospective synergistic or antagonistic interactions with thymol vis-a-vis growth inhibition of the test strains. Lauric acid and myristic acid each behaved synergistically with thymol to inhibit the growth of at least one test strain, whereas cis-10-heptadecenoic acid and thymol were noticeably antagonistic towards the growth of *S. sobrinus*.

The animal or individual in all of the methods of the present subject matter disclosed above may be a mammal such as a mouse, rat, cat, dog, horse, cow, or other domesticated animal, or a human. In a certain embodiment, the animal is human. In addition to uses for treating human diseases, disorders, and conditions, the methods of the present subject matter may have veterinary applications. The compositions of the present subject matter, which contain certain fatty acids, may thus be useful for treating or preventing the conditions described above and may improve the wellness of an individual in regards to avoiding the onset or severity of the above diseases and disorders.

Routes of Administration

In a certain embodiment, an orally administered composition is in the form of one or more capsules, one or more tablets, or one or more pills.

The subject compositions are delivered to the patient by means of a pharmaceutically acceptable carrier. Such carriers are well known in the art and generally will be in either solid or liquid form. Solid form herbal preparations which may be prepared according to the present subject matter include powders, tablets, dispersible granules, capsules, cachets and suppositories. In general, solid form preparations will comprise from about 5% to about 90% by weight of the active agent.

A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the viscous active compound. In tablets, the active compound is mixed with a carrier having the necessary binding properties in suitable proportions and compacted to the shape and size desired. Suitable solid carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating materials as a carrier which may provide a capsule in which the active component (with or without other carriers) is surrounded by carrier, which is thus in association with it. Similarly, cachets are included. Tablets, powders, cachets, and capsules can be used as solid dosage forms sui table for oral administration. If desired for reasons of convenience or patient acceptance, pharmaceutical tablets prepared according to the present subject matter may be provided in chewable form, using techniques well known in the art.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions for parenteral injection, the liquid preparations may include water or water/propylene glycol solutions. Liquid preparations can also be formulated in solution in aqueous polyethylene glycol solution. Aqueous solutions suitable for oral use can be prepared by dissolving the active component in water and adding sui table colorants, flavors, stabilizers and thickening agents as desired. Aqueous suspensions suitable for oral use can be made my dispersing the finely divided active component in water with a viscous material, i.e., natural or synthetic gums, resins, methylcellulose, sodium carboxymethylcellulose, and other well known suspending agents. Liquid pharmaceutical preparations may comprise up to 100% by weight of the subject active agent.

Solid form preparations which are intended to be converted, shortly before use, to liquid form preparations for either oral or parenteral administration are also contemplated as suitable carriers. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing useful liquid form preparations may be water, isotonic water, ethanol, glycerine, propylene glycol, and the like as well as mixtures thereof. In one embodiment, the liquid form may be prepared in the form of a capsule, such as a gelatin capsule comprising glycerine and water, containing the combined polyunsaturated oil and herbal composition.

Naturally, the liquid utilized will be chosen with regard to the route of administration. For example, liquid preparations containing large amounts of ethanol are not suitable for parenteral use.

The herbal preparations of the present subject matter may include one or more preservatives well known in the art, such as benzoic acid, sorbic acid, methylparaben, propylparaben and ethylenediaminetetraacetic acid (EDTA). Preservatives are generally present in amounts up to about 1% and preferably from about 0.05 to about 0.5% by weight of the pharmaceutical composition.

Useful buffers for purposes of the present subject matter include citric acid-sodium citrate, phosphoric acid-sodium phosphate, and acetic acid-sodium acetate in amounts up to about 1% and preferably from about 0.05 to about 0.5% by weight of the pharmaceutical composition. Useful suspending agents or thickeners include cellulosics like methylcellulose, carageenans like alginic acid and its derivatives, xanthan gums, gelatin, acacia, and microcrystalline cellulose in amounts up to about 20% and preferably from about 1% to about 15% by weight of the pharmaceutical composition.

Sweeteners which may be employed include those sweeteners, both natural and artificial, well known in the art. Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof may be utilized in amounts from about 10% to about 60% and preferably from about 20% to about 50% by weight of the pharmaceutical composition. Water soluble artificial sweeteners such as saccharin and saccharin salts such as sodium or calcium, cyclamate salts, acesulfame-K, aspartame and the like and mixtures thereof may be utilized in amounts from about 0.001% to about 5% by weight of the composition.

Flavorants which may be employed in the herbal products of the present subject matter include both natural and artificial flavors, and mints such as peppermint, menthol, artificial vanilla, chocolate, artificial chocolate, various fruit flavors, both individually and mixed, vanilla, cinnamon, in amounts from about 0.5% to about 5% by weight of the pharmaceutical composition.

Colorants useful in the present subject matter include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, known as F.D.&C. dyes and the like. Such dyes are generally present in amounts up to about 0.25% and preferably from about 0.05% to about 0.2% by weight of the pharmaceutical composition. A full recitation of all F.D.&C. and D. &C. dyes and their corresponding chemical structures may be found in the Kirk-Othmer Encyclopedia of Chemical Technology, in Volume 5, at pages 857-884, which text is accordingly incorporated herein by reference.

Useful solubilizers include alcohol, propylene glycol, polyethylene glycol and the like and may be used to solubilize the flavors. Solubilizing agents are generally present in amounts up to about 10%; preferably from about 2% to about 5% by weight of the pharmaceutical composition.

Lubricating agents which may be used when desired in the instant compositions include silicone oils or fluids such as substituted and un substituted polysiloxanes, e.g., dimethyl polysiloxane, also known as dimethicone. Other well known lubricating agents may be employed.

The herbal preparation may also be prepared in a unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

It is not expected that compounds of the present subject matter will display significant adverse interactions with other synthetic or naturally occurring substances. Thus, a compound of the present subject matter may be administered in combination with other compounds and compositions useful, for example, for treating cancer. In particular the compounds of the present subject matter may be administered in combination with other compounds of the present subject matter, chemotherapeutic substances, and so forth.

The desired herbal formulations will be determined by one skilled in the art depending upon considerations such as the route of administration and desired dosage. See, for example, "Remington's Pharmaceutical Sciences", 18th ed. (1990, Mack Publishing Co., Easton, Pa. 18042), pp. 1435-1712, the disclosure of which is hereby incorporated by reference. Such formulations may influence the physical state, stability, rate of in vivo release, and rate of in vivo clearance of the present therapeutic agents of the present subject matter.

Dosage

Dosage levels on the order of about 0.001 mg to about 100 mg per kilogram body weight of the active ingredient compounds or compositions are useful in the treatment of the conditions described herein. In one embodiment, the preferred total dosage ranges from 200 mg per day to 2000 mg per day per individual. Other embodiments include daily doses of >2000 mg per day per individual. The compounds and compositions of the present subject matter may usually be given in two or three doses daily. Starting with a low dose (200-300 mg) twice daily and slowly working up to higher doses if needed is a contemplated strategy. The amount of active ingredient that may be combined with the carrier materials to produce a single dosage form will vary depending upon the host treated and the particular mode of administration. In one embodiment, a single dosage unit comprises 1000 mg of the composition of the present subject matter in a single capsule, and a single capsule is administered twice per day for a total dose of 2000 mg per day.

It is understood, however, that a specific dose level for any particular patient will depend upon a variety of factors, including the activity of the specific compound employed; the age, body weight, general health, sex and diet of the patient; the time of administration; the rate of excretion; drug combination; the severity of the particular disorder being treated; and the form of administration. One of ordinary skill in the art would appreciate the variability of such factors and, except where unexpected results are indicated, would be able to establish specific dose levels using no more than routine experimentation.

EXAMPLES

The following examples are illustrative of the present subject matter and are not intended to be limitations thereon. Unless otherwise indicated, all percentages are based upon 100% by weight of the final composition. The use of the term "WholeMega" refers to the compositions of the present subject matter, the compositions comprising a therapeutically effective amount of supercritical extract of rosemary, and a supercritical extract of oregano, in combination with a polyunsaturated oil composition.

Example: 1: Clinical Study with Present Compositions (WholeMega Compositions): Absorption of the Salmon Oil Lipids A clinical study was conducted in human volunteers who consumed 2 g or 4 g of the WholeMega salmon oil product, a composition of the present subject matter. The presence of major fish oil lipids in serum was determined over time. Results showed that WholeMega lipids absorbed across the gut membrane and were detectable in serum.

Figure 2:
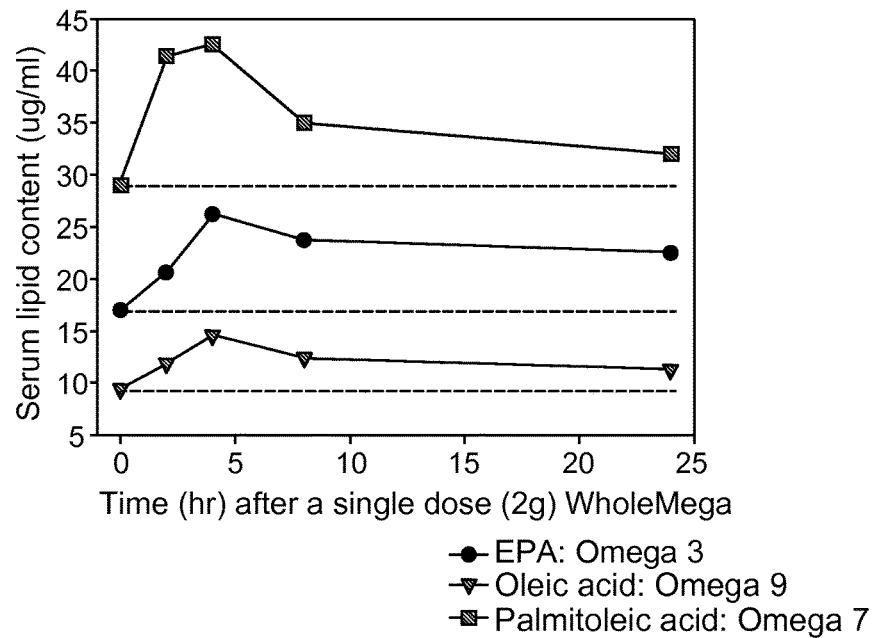
FIG. 2. Human volunteers (n=8) were administered a 2 g dose of WholeMega and serial blood samples were obtained for lipid analyses. The time-dependent changes in mean EPA, oleic and palmitoleic acids (which are representative of WholeMega omega-3, -5, and -7 polyunsaturated fatty acids, respectively) are depicted in the figure. Changes in omega 3 (EPA), omega 7 (palmitoleic acid) and omega 9 (oleic acid) are plotted to demonstrate the breadth of changes in lipid classes. The dashed lines merely indicate baseline (pre-dose) levels. The persistence of changes in WholeMega-derived lipids for up to 24 hours can be seen.

The results clearly showed absorption of the WholeMega salmon oil lipids and their appearance in serum. Consumption of 2 g or 4 g doses of WholeMega produces concentration- and time dependent changes in serum EPA omega-3 content as shown in FIGS. 1 and 2. The composition of the present subject matter also produces time-dependent changes in mean EPA, oleic and palmitoleic acids (which are representative of WholeMega omega-3, -5, and -7 polyunsaturated fatty acids, respectively) are depicted in FIG. 2. Changes in omega 3 (EPA), omega (palmitoleic acid) and omega 9 (oleic acid) demonstrate the breadth of changes in lipid classes. The dashed lines merely indicate baseline (pre-dose) levels. The persistence of changes in WholeMega derived lipids for up to 24 hr can be seen. In other embodiments, other compositions of the present subject matter are also useful for attaining these changes in lipid composition.

Example: 2: Incorporation of Polyunsataurated Lipids into Cell Membranes

Figure 3:
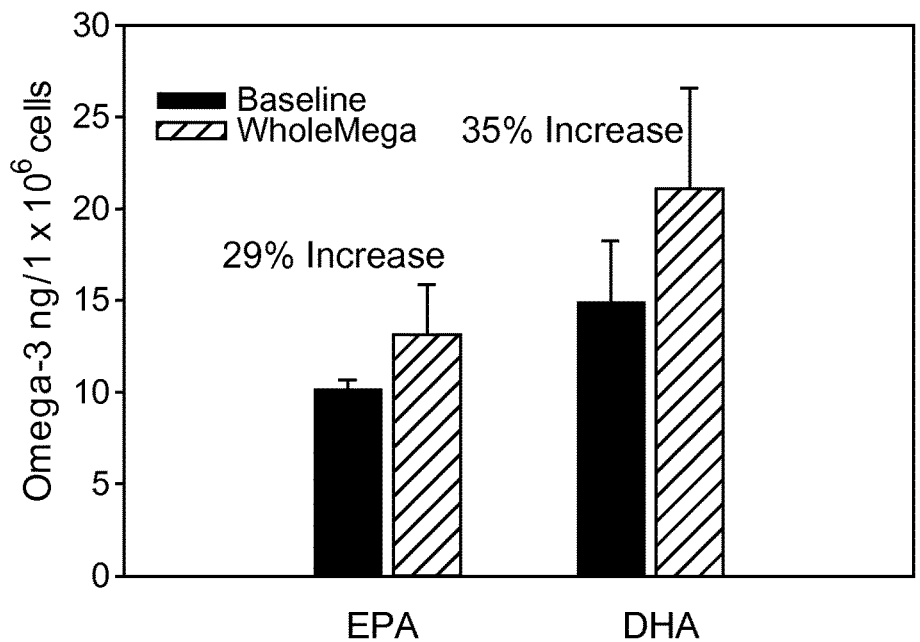
FIG. 3. Change in cell (PEMC) membrane content of omega-S 3 lipids (top) and omega-7 and omega-9 lipids (bottom) after consumption of WholeMega (2 g). Subjects received a dose of 2 g of WholeMega daily for 3 days. Differences in cell membrane lipid composition were compared between those at predose and 24 hr following administration of the third and final dose.
Figure 3:
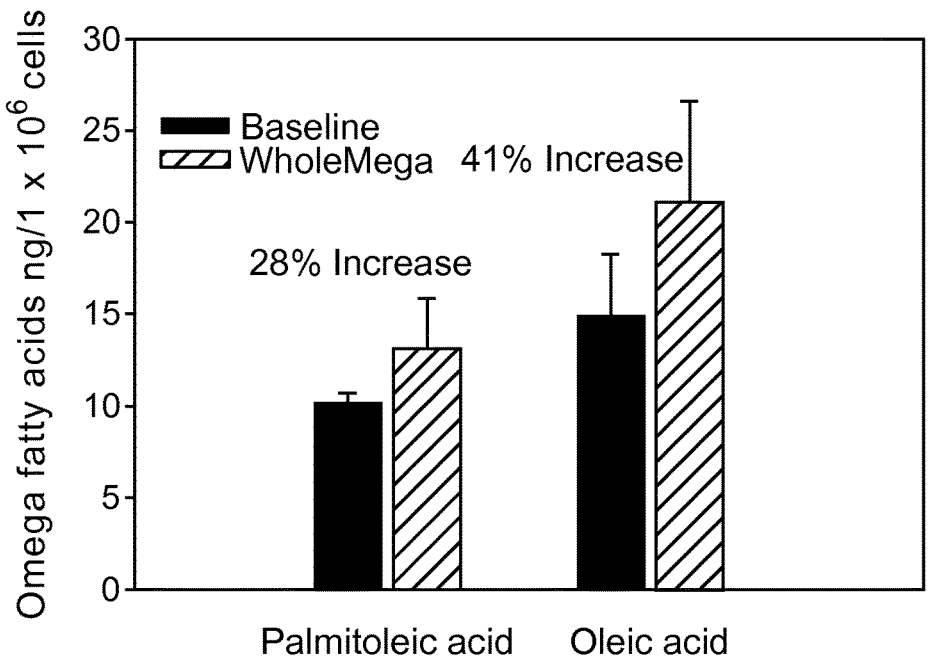

To assess whether cell membrane lipid composition was altered after consumption of a composition of the present subject matter, samples of peripheral blood mononuclear cells (PEMCs) were obtained pre- and post dosing and membrane lipid content was measured by GC/MS. As shown in FIG. 3 below, even a single 2 g dose of WholeMega resulted in easily demonstrable increases in membrane composition of WholeMega derived lipids. Data were obtained from four volunteers who took WholeMega (2 g/day) for three consecutive days. The difference in membrane lipid composition predose and after the third daily dosing was determined.

Example: 3: WholeMega Improves the Ratio of 'Good Lipids' to 'Bad Lipids'

Figure 4:
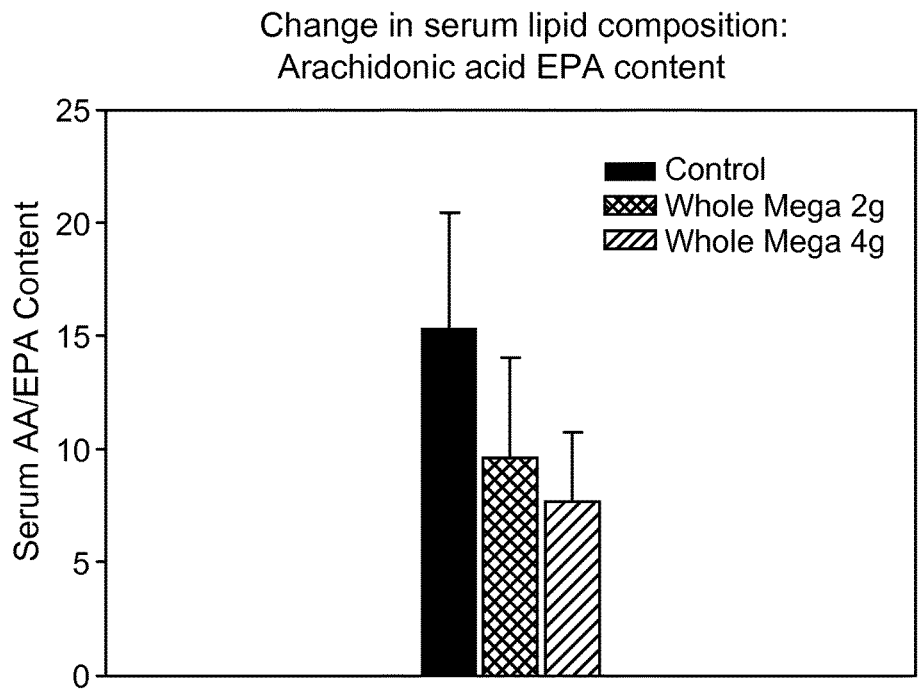
FIG. 4. Consumption of WholeMega at either 2 or 4 grams results in an easily detectable shift in AA/EPA ratios in blood. A 2 9 dose results in an average 37% decline in this ratio while a 4 9 dose results in an average 50% decline in serum AA/EPA ratio. Data were derived from 8 subjects consuming 2 9 WholeMega and 5 subjects consuming 4 9 WholeMega as a single serving. Data are presented as Mean+/−SE.
Figure 5:
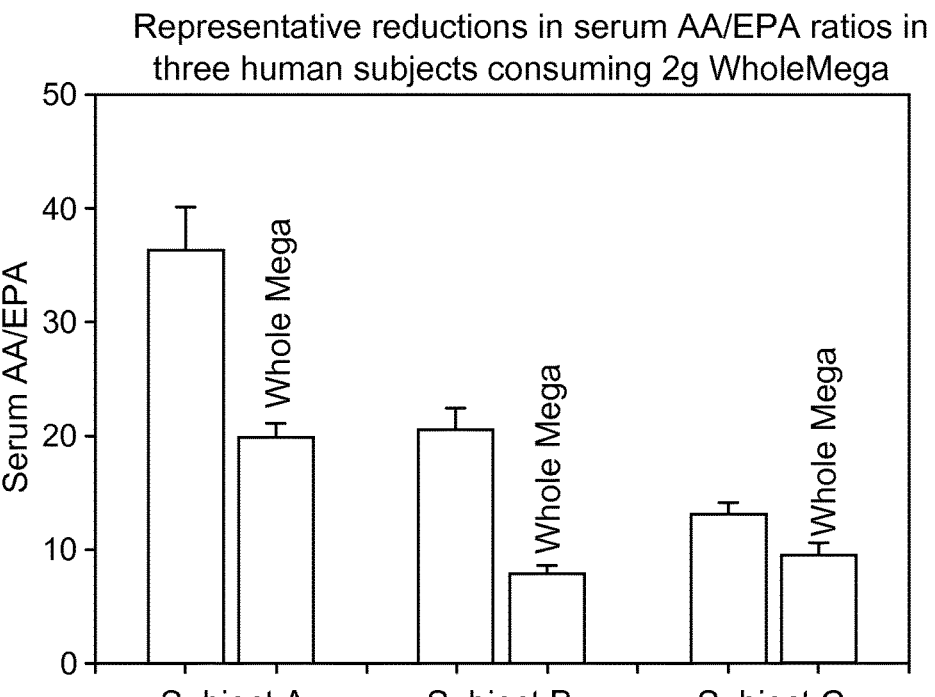
FIG. 5. Examples of the shift in serum AA/EPA ratios within individuals who consumed WholeMega are shown in the graph above. Data are shown as Mean+/−SE. All WholeMega values are significantly ($p<0.05$) different from preRx values.

The change in serum lipid content after WholeMega resulted in an increase in healthy omega-3 oils, such as EPA, and a relative fall in the omega-6 oil arachidonic acid (AA) This change in omega-6 to omega-3, or AA/EPA, ratios was dose dependent as shown in FIG. 4. and FIG. 5. Such a change is considered beneficial for health and reduces the inflammatory potential.

Figure 6:
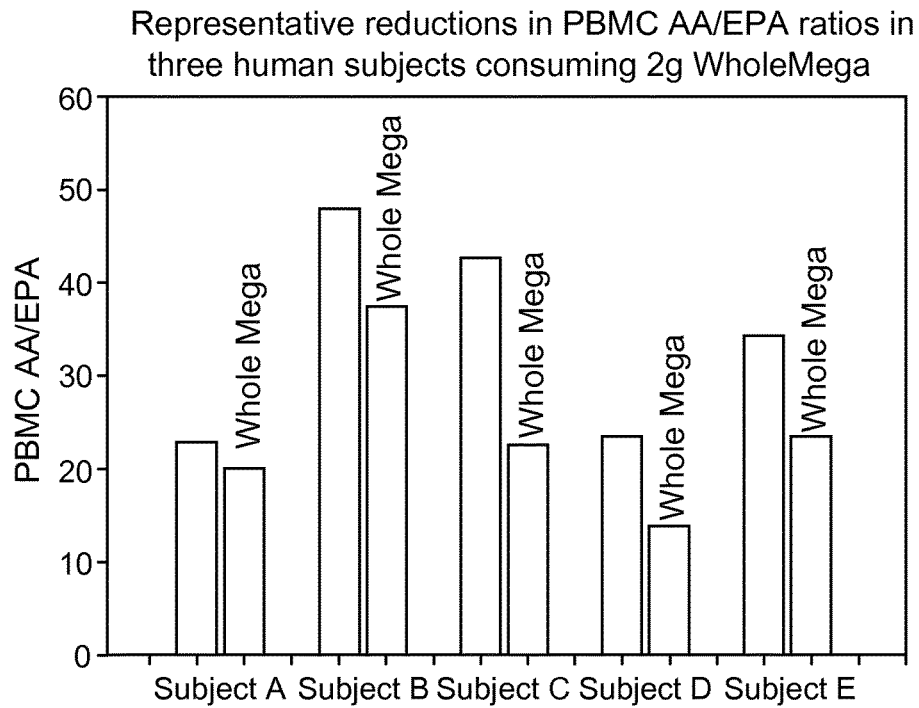
FIG. 6. WholeMega consumption at either 2 9 or 4 9 per day results in a change in peripheral blood mononuclear cell membrane composition. Membrane arachidonic acid is reduced as a consequence of greater incorporation of EPA derived from WholeMega. The importance of this plot is that even with 2 g/day of WholeMega one can achieve a heal thy shift in tissue (white blood cell) membrane composition and reduce the potential for inflammation derived from arachidonic acid. The plots above were derived from data obtained from 4 subjects who took WholeMega for 3 consecutive days at 2 g/day. Peripheral blood mononuclear cells were obtained predose and 3 days after dosing with WholeMega. Cell membrane lipid composition in terms of content of the important omega-3 fatty acid, EPA, is increased.

Similarly, FIG. 6. shows WholeMega consumption at either 2 g or 4 g per day results in a change in peripheral blood mononuclear cell membrane composition. Membrane arachidonic acid is reduced as a consequence of greater incorporation of EPA derived from WholeMega. The importance of this plot is that even with 2 g/day of WholeMega one can achieve a healthy shift in tissue (white blood cell) membrane composition and reduce the potential for inflammation derived from arachidonic acid. The plots above were derived from data obtained from 4 subjects who took WholeMega for 3 consecutive days at 2 g/day. Peripheral blood mononuclear cells were obtained predose and 3 days after dosing with WholeMega. Cell membrane lipid composition in terms of content of the important omega-3 fatty acid, EPA, is increased.

Another way to assess the impact of a nutritional supplement such as fish oil is to determine the shift in "good fats" relative to "bad fats" in serum and tissue membranes. The classification of 'good' and 'bad' fats, is based on what is known about the consequences of these particular fatty acids. See the discussion above for a relative classification of fats.

Examination of the relative changes in the Good Fats/Bad Fats ratio revealed a shift, albeit minor, in this ratio for both serum and tissue membrane composition in those individuals consuming a 2 g dose of WholeMega. Even though a 5-10% shift in the ratio is small numerically, there are important health consequences as a result of even this small a shift in the 'good fat'/'bad fat' ratio.

TABLE V

| Group | Pre-dose: "Good Fats"/"Bad Fats" | Post-dose: "Good Fats"/"Bad Fats" | Change (%) |
| --- | --- | --- | --- |
| Serum | 1.76 +/− 0.18 | 1.91 +/− 0.16 | 8.5% Increase |
| Tissue (PBMC) | 0.54 +/− 0.03 | 0.59 +/− 0.04 | 9.2% Increase |

Data in Table V reflect changes in ratios of "Good Fats"/"Bad Fats" recorded from analyses of data from 8 volunteers who consumed 2 g WholeMega. Changes in PBMC membrane composition of "Good Fats"/"Bad Fats" are derived from data of 4 individuals who consumed WholeMega (2 g/day) for three consecutive days. Data are presented as Mean+/−SE. In another embodiment, a composition of the present subject matter increases the ratio of "Good Fats"/"Bad Fats" in serum by at least 5.0%, at least 6.0%, 5 at least 6.5%, at least 7.5%, at least 8.0%, or at least 8.5%; or in tissue by at least 5.0%, at least 6.0%, at least 6.5%, at least 7.5%, at least 8.0%, at least 8.5%, or at least 9.2%.

Example: 4: WholeMega Improves Blood Lipid Chemistries 10 Associated with Good Cardiovascular Health Blood chemistry analyses are important not only for the things that change but also for those that do not change (e.g. IgE for fish oil). Here are evaluations of important differences in blood chemistries due to WholeMega. Data are from 4 individuals who received WholeMega at 2 gm/day for 3 continuous days. While the limited data sets are not capable of providing sufficient information for statistical analyses they clearly show a trend of beneficial changes in serum blood chemistries that are relevant to good health. An examination of such blood lipid chemistries over a longer dosing period (e.g. 2-4 weeks) would be of interest.

TABLE V

| Data | Pre-dose/Post-dose | Percent Change | Range |
| --- | --- | --- | --- |
| C-RP (HS) | 1.07/0/9 | 15.9%↓ | 0-46.4% |
| LDL "Bad Cholesterol" | 172.4/149.3 | 13.4%↓ | 4.5-21.6% |
| Triglycerides | 170.6/150.2 | 11.9%↓ | 8.5-18.0% |
| Cholesterol | 246.5/226 | 8.3%↓ | 0-14% |
| Cholesterol/HDL | 5.7/5.3 | 7.0%↓ | 1.1-12.3% |

Changes in triglycerides, cholesterol, and LDL have been noted previously by others with administration of high doses of fish oil. In this example, however, changes in triglycerides and LDL were unexpectedly obtained only after administration of the relatively low dose of 2 gm/day. This is unexpected because previous studies of fish oil have not reported a change in cholesterol at any dose. A small but meaningful fall in total cholesterol levels was observed. This is also reflected in the small fall in cholesterol/HDL ratio which one wants to see as low as possible.

It has recently been reported in the *European Journal of Clinical Nutrition* (epub, ahead of actual publication), authors M. A. Micallef et al report that levels of C-reactive protein (CRP), a marker of inflammation and reported to be independent predictor of cardiovascular-related events, are inversely related to blood levels of DHA and EPA. Data using compositions of the present subject matter are consistent with this report.

Example: 5: WholeMega does not Significantly Change Levels 20 of Cytokines and/or Chemokines Early analyses of cytokine and chemokine data indicate no significant changes that can be attributed to administration of a single or even multiple doses of WholeMega. In hindsight, this result is not unexpected because this is not known to occur with acute dosing of fish oil. In some embodiments, fish oil may modulate inflammation once it has occurred or dampen responses to stimuli that cause inflammation (i.e. prevention) without significantly changing the cytokines measured in this study.

Example 6: WholeMega is Acceptable for Human Consumption

Assessment of human acceptability of the WholeMega product was considered by STT (our CRO) to be good. There were few drop outs and of these only one complained about the fish burp phenomenon.

Example 7: Fish Oil Diets and Lung Cancer

Figure 7:
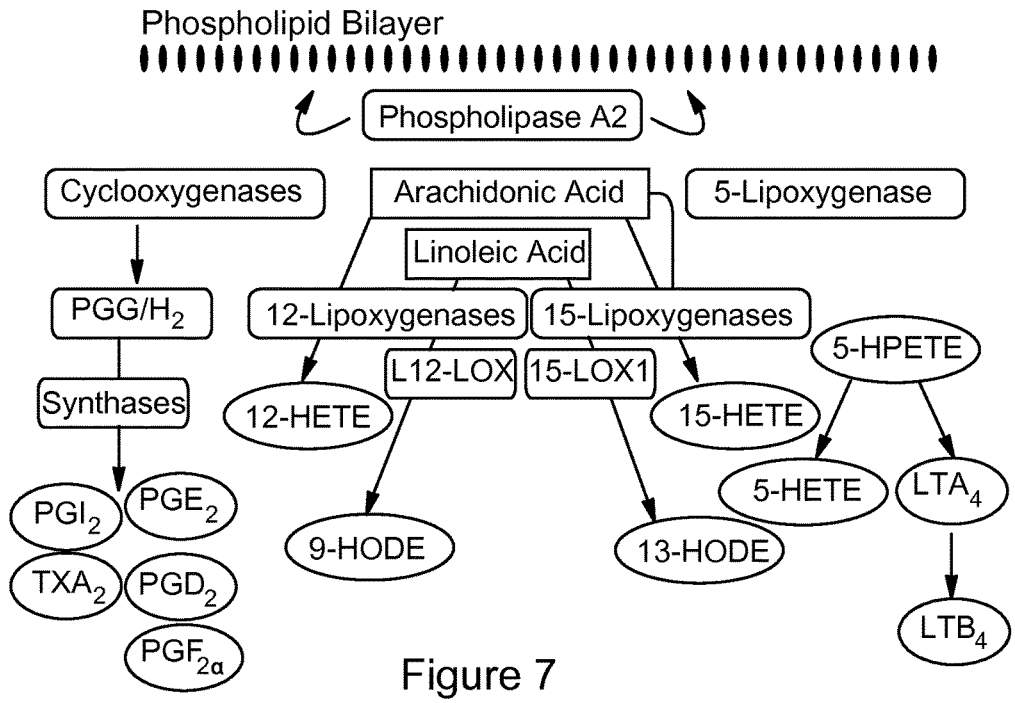
FIG. 7. Schematic diagram showing the metabolism of arachidonic acid liberated from cell membranes by action of phospholipase. The released arachidonic acid serves as a substrate for cyclooxygenase and lipoxygenase enzymes which convert it to lipid products (such as eicosanoids) that are responsible for inflammation.
Figure 8:
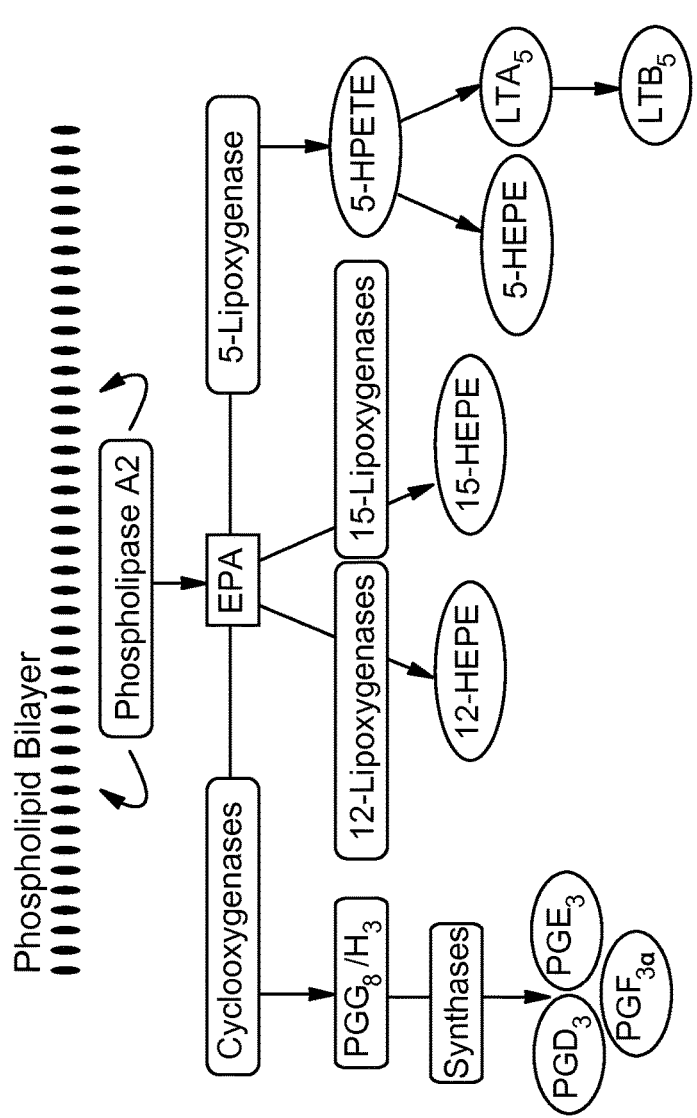
FIG. 8. Schematic diagram of the role that certain polyunsaturated fatty acids such as EPA have in the reduction of inflammatory lipids. Oils such as EPA from fish become incorporated into the cell membrane where they are liberated upon activity of the enzyme phospholipase. The released EPA serves as a substrate for cyclooxygenase and lipoxygenase enzymes but the products that are produced are greatly reduced in inflammatory potential compared to that produced by arachidonic acid.

In summary, in vitro studies described herein indicate that n-6 polyunsaturated fatty acids promote the growth of tumor cells and that n-3 polyunsaturated lipids (such as EPA) inhibit the proliferation of human lung cancer cells. It is thought that this effect is mediated in part through COX-2 metabolism. See FIGS. 7 and 8 for a representation of various lipid metabolism pathways involved with cyclooxygenases, lipoxygenases, lipid messengers, and membrane composition.

Fish oil n-3 diets are known to have anti-inflammatory effects, provide cardiovascular protection, provide immune modulation and augment the cytotoxic effects of chemotherapy.

Possible molecular mechanisms responsible for anticancer activity of n-3 fatty acids have been postulated (Hardman, E. J. Nutr. 132: 3508S, 2002). These include, for example, n-3 lipids and lipids derived from them through metabolism induce differentiation of cancer cells; suppress NFKB activation and Bcl-2 expression; decrease the expression of AP-1 and Ras; reduce cancer-associated cachexia; and alter eicosanoid metabolism and inhibit production of PGE2.

Example 8: Prostate Cancer Clinical Study Experimental Design a case-control study with 466 men diagnosed with aggressive prostate cancer and 478-age and ethnicity-matched controls.

Genotype analysis: nine COX-2 tag single nucleotide polymorphisms (SNP).

Results: Increasing intake of LC n-3 was strongly associated with a decreased risk of aggressive prostate cancer ($p<0.0001$). This reverse association was even stronger among men with particular COX-2 variant SNP (SNP rs4648310).

Conclusion: Dietary intake of LC n-3 fatty acids may reduce inflammation and in turn decrease risk of prostate cancer development and progression. This potential effect may be modified by genetic variation in COX-2, a key enzyme in fatty acid metabolism and inflammation Example 9: Cyclooxygenase-2 and Lung Cancer Elevated COX-2 expression and PGE2 formation has been found in most non-small cell lung cancers, including preinvasive precursor lesions and invasive lung carcinoma. PGE2 promotes proliferation and angiogenesis and prevents apoptosis of NSCLC cells by up-regulation of BCl-2, Src, MAPK, VEGF, EGF and down-regulation of BAX signaling pathways. Treatment of humans with the selective COX-2 inhibitor celecoxib or NSAIDs augment the anti-tumor effects of chemotherapy in patients with non-small cell lung cancer.

PGE2 slightly stimulates proliferation of A549 cells, whereas PGE3 inhibits proliferation of these particular cells Anti-proliferative activity of EPA is associated with PGE3 formation in non-small lung cancer (NSLC) cell line A549. PGE2 is derived from arachidonic acid, a "bad fat". PGE3 is derived from EPA, a "good fat". Experiments were conducted to determine if diets having altered ratios of good fats to bad fats differentially impact the development of human lung cancer.

Example 10: Comparing COX-2 Expression Systems in Cancer

The antitumor efficacy of specifically formulated fish oil 30 diets was studied in human lung cancer A549 xenograft (over expression of COX-2) and H1299 xenograft (lack of COX-2 expression).

Figure 9:
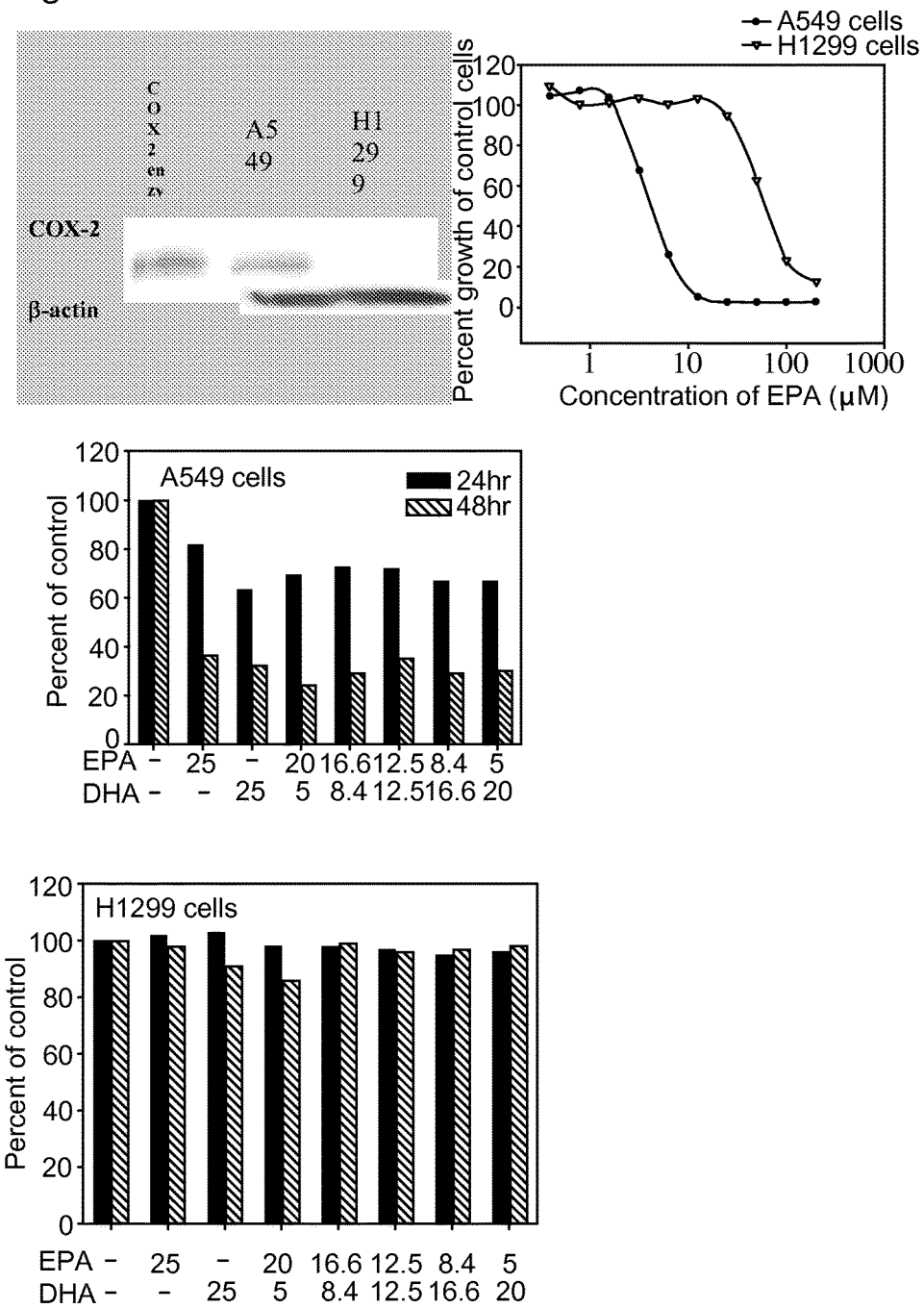
FIG. 9. The antitumor efficacy of specifically formulated fish oil diets was studied in human lung cancer A549 xenografts (over expression of COX-2) and H1299 xenograft (lack of COX-2 expression). EPA inhibits the proliferation of A549 cells but not H1299 cells.

EPA inhibits the proliferation of A549 cells but not H1299 cells. See FIG. 9.

Figure 10:
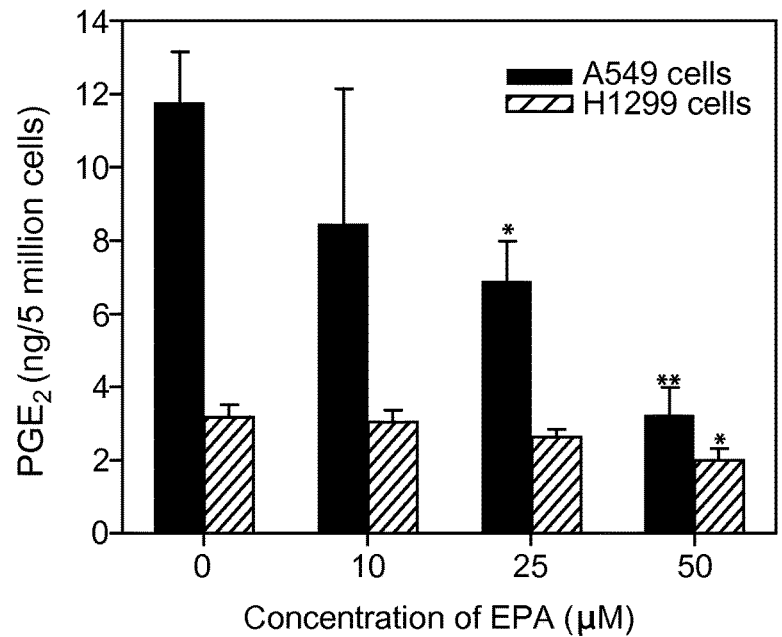
FIG. 10. The antitumor efficacy of specifically formulated fish oil diets was studied in human lung cancer A549 xenografts (over expression of COX-2) and H1299 xenograft (lack of COX-2 expression). Production of PGE2 and PGE3 in human lung cancer A549 and H1299 cells exposed to EPA (Yang, P. et al. J. Lipid Res. 2004).
Figure 10:
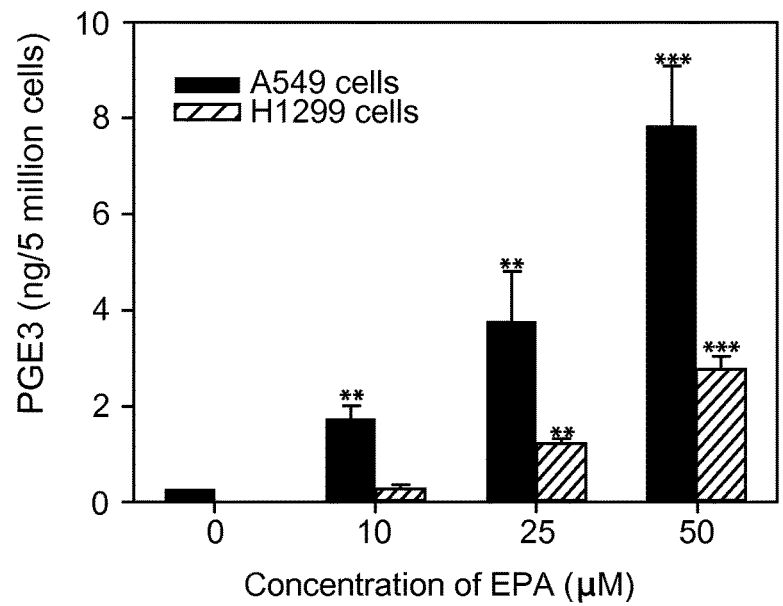

Production of PGE2 and PGE3 in human lung cancer A549 and H1299 cells exposed to EPA (Yang, P. et al. J. Lipid Res. 2004). 5 EPA inhibits COX-2 mediated synthesis of PGE2 in A549 cells which contain COX-2 but not in H1299 cells which are lacking significant COX-2 expression. EPA also gives rise to production of the relatively less inflammatory PGE3 in A549 cells and to a lesser extent in H1299 human non small cell lung cancer cells. See FIG. 10.

Figure 11:
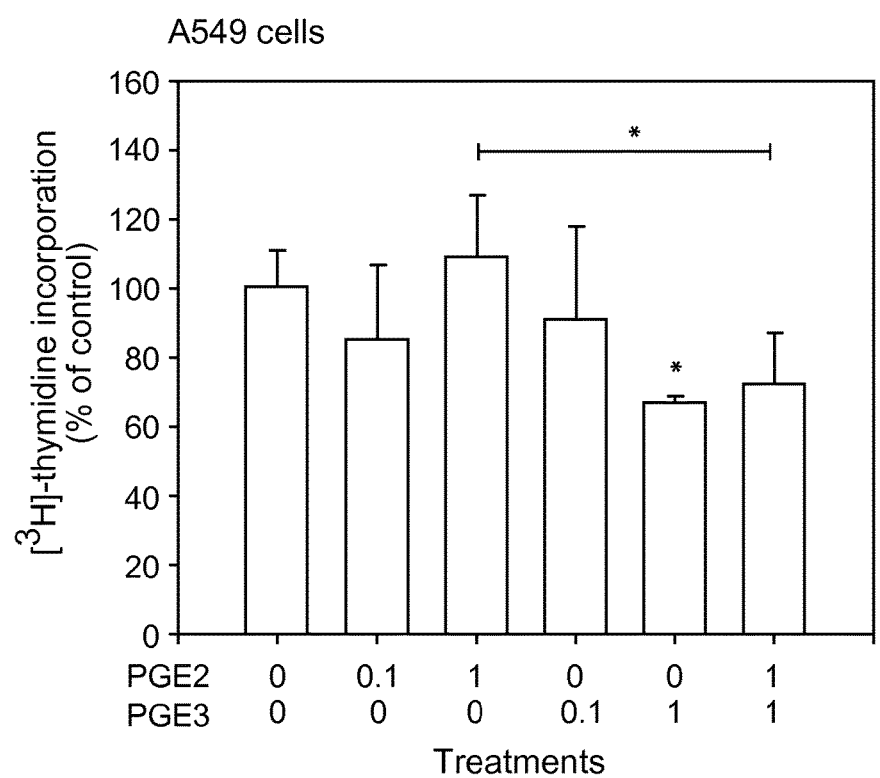
FIG. 11. PGE2 slightly stimulates proliferation of A549 cells, whereas PGE3 inhibits proliferation of these particular cells.

PGE2 slightly stimulates proliferation of A549 cells, whereas PGE3 (derived from fish oil EPA) inhibits proliferation of these particular cells. See FIG. 11.

Figure 12:
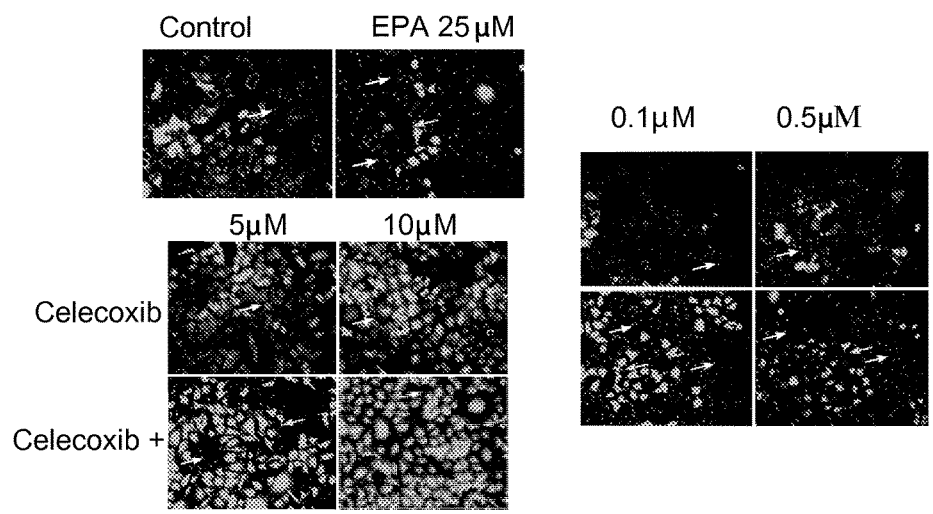
FIG. 12. Anti-proliferative activity of EPA is associated with PGE3 formation in A549 cells.
Figure 12:
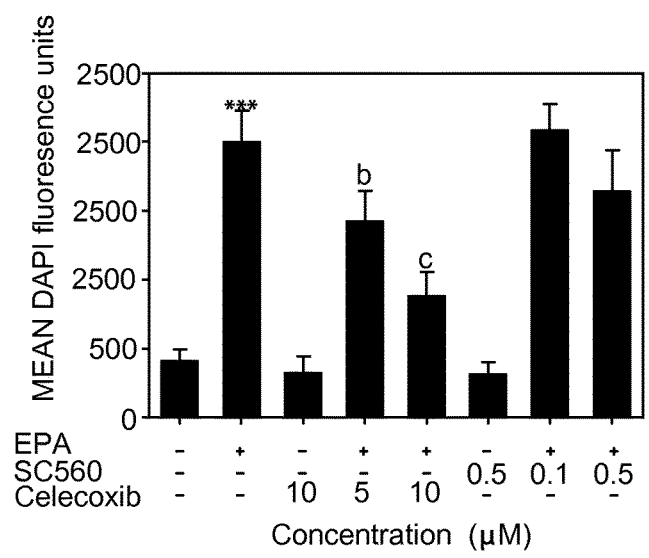

Anti-proliferative activity of EPA is associated with PGE3 formation in A549 cells. The arrows in FIG. 12 point to apoptotic dying cells, an effect produced in these human nonsmall cell lung cancer cells by incubation with fish oil EPA. The data also show that this effect is due to inhibition of COX-2 and not COX-I. The use of the selective COX-2 inhibitor, celecoxib, largely negates the anti-proliferative effect of EPA. See FIG. 12.

Figure 13:
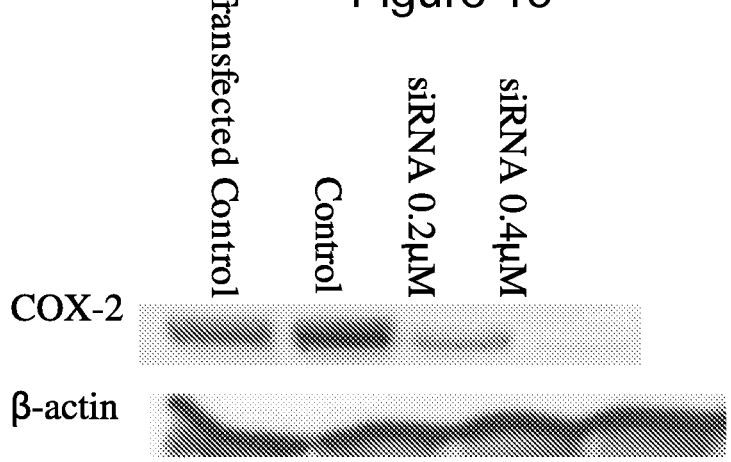
FIG. 13. The anti-proliferative effect of EPA was reduced in A549 cells transfected with COX-2 siRNA that blocks expression of this enzyme (COX-2) in cells.
Figure 13:
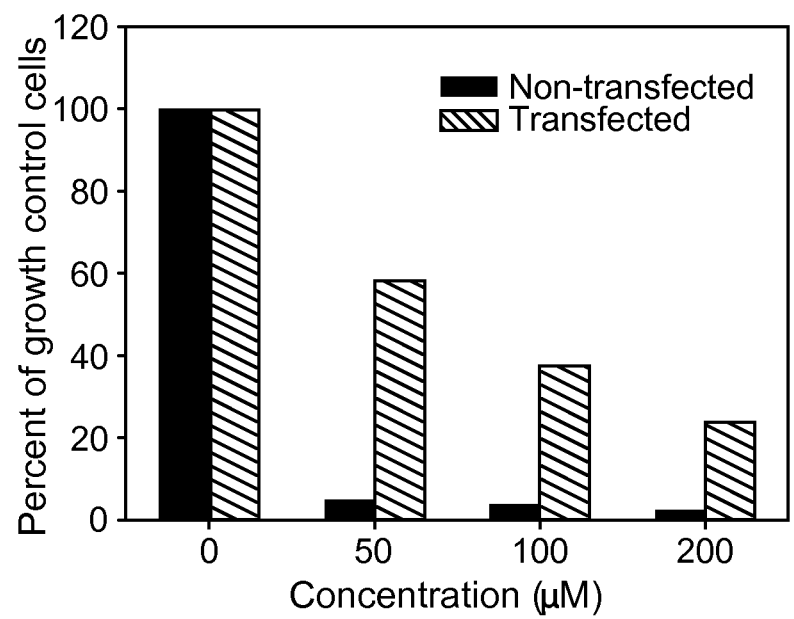

The anti-proliferative effect of EPA was reduced in 4549 cells transfected with COX-2 siRNA. That is, blocking the production and expression of COX-2 blocked the formation of epa derge3 and thus the anti-proliferative effect of this fish oil. See FIG. 13.

In summary, these in vitro studies suggest that EPA inhibits the proliferation of human lung cancer cells mediated through COX-2 metabolism.

Example 11: Products Comparing Effects of Different Fish Oil

Figure 14:
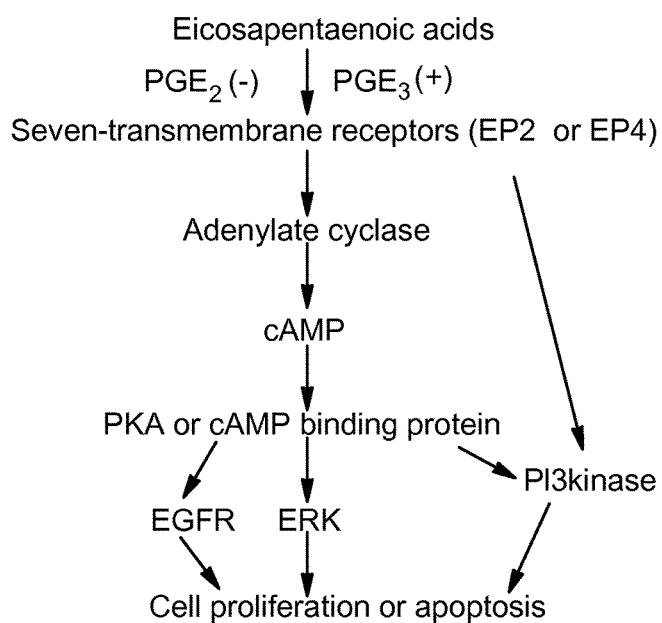
FIG. 14. Examples of possible mechanisms of the metabolism of Fish Oil derived PGE3 in lung cancer.
Figure 15:
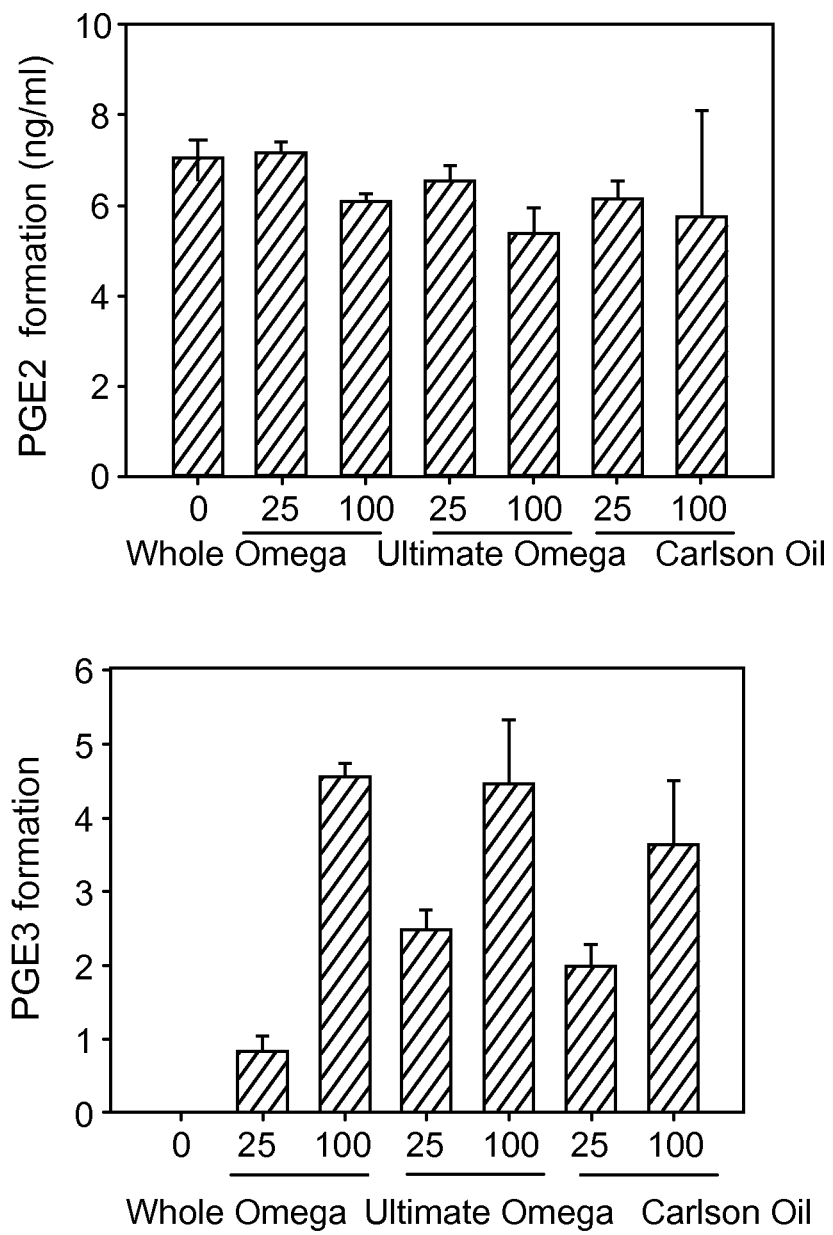
FIG. 15. Formation of PGE2 and PGE3 was studied in A549 cells treated with three different fish oil products—WholeMega (a composition of the present subject matter); Nordic Natural Ultimate Omega, and Carlson Oil. Comparison is shown of formation of PGE2 and PGE3 in A549 cells treated with different fish oils and was made by using equal amounts (pg/ml) of these fish oil products.

Examples of possible mechanisms of the metabolism of Fish Oil derived PGE3 in lung cancer are shown in FIG. 14. Formation of PGE2 and PGE3 was studied in A549 cells treated with three different fish oil-derived products: WholeMega (a composition of the present subject matter); Ultimate Omega; and Carlson Oil. See FIG. 15, the comparison of formation of PGE2 and PGE3 in A549 cells treated with different oil compositions was made by using equal amounts (pg/ml) of each oil.

Figure 16:
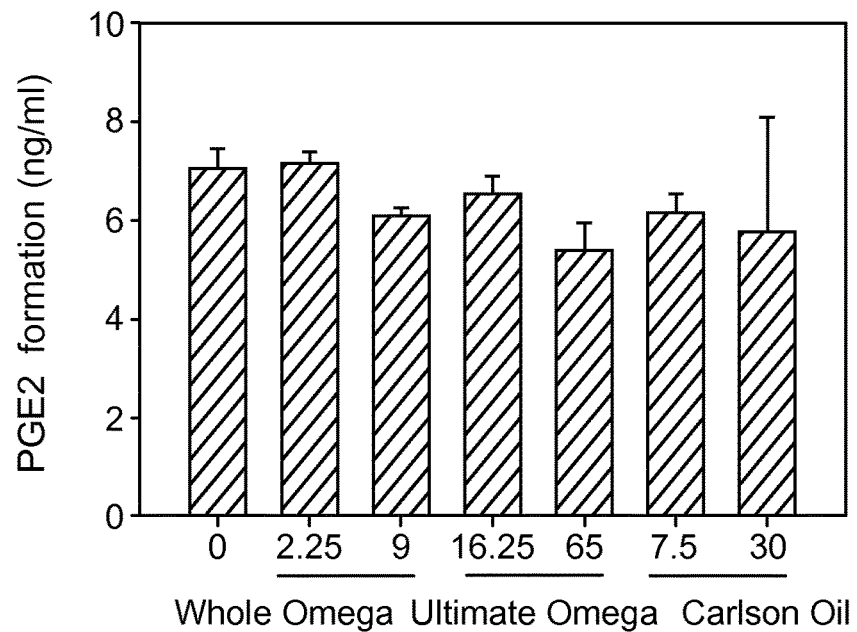
FIG. 16. Comparison is shown of formation of PGE2 and PGE3 in A549 cells treated with different fish oils and was made by using different amounts (pg/ml) of EPA in fish oil products.
Figure 16:
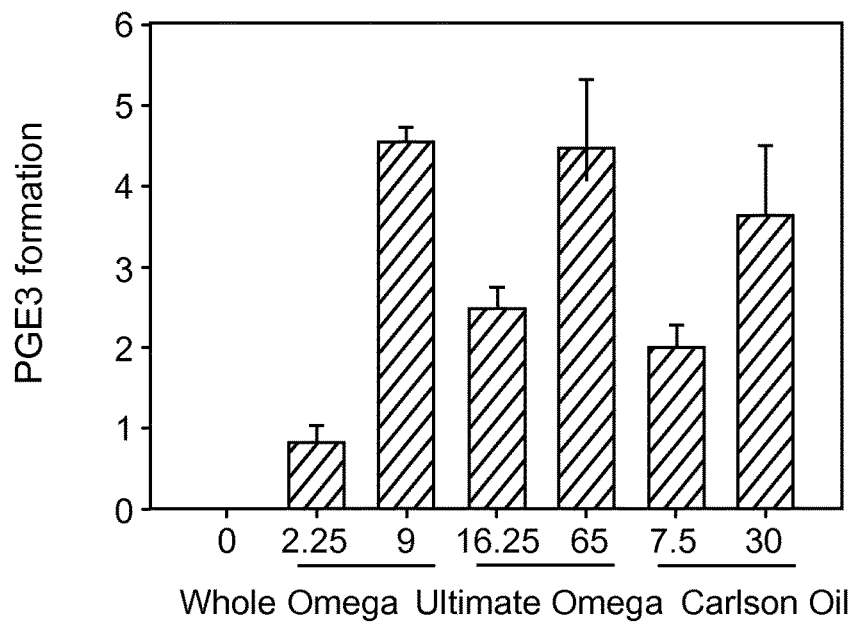

The comparison of formation of PGE2 and PGE3 in A549 cells treated with different fish oil products was made by using different amounts (pg/ml) of EPA in fish oil. The greater potency of WholeMega vs the other two commercial fish oils with respect to formation of the anti-inflammatory PGE3 is apparent. See FIG. 16.

Figure 17:
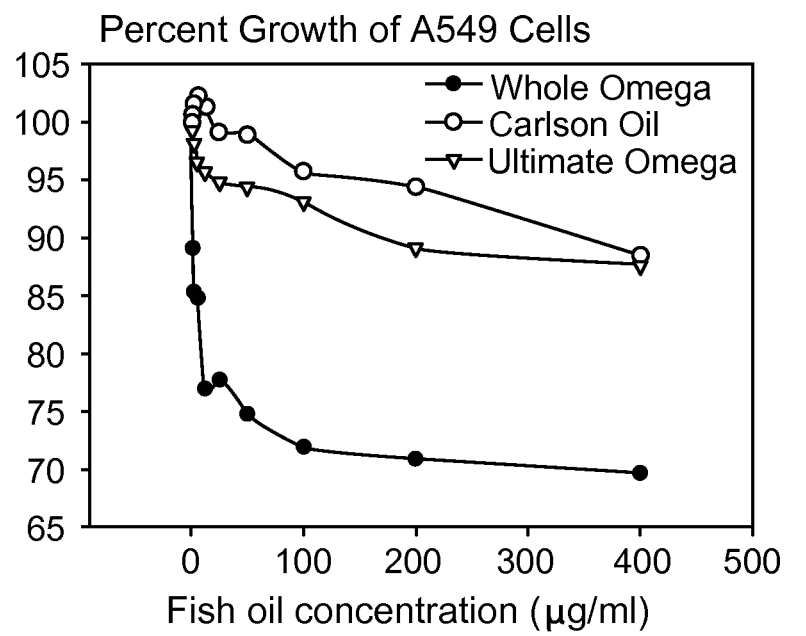
FIG. 17. Anti-proliferative effect of fish oils in A549 and H1299 human nonsmall cell lung cancer cells is shown. A composition of the present subject matter (WholeMega) unexpectedly provided substantially superior results to the other fish oil compositions in cancer cells where COX-2 was over expressed.
Figure 17:
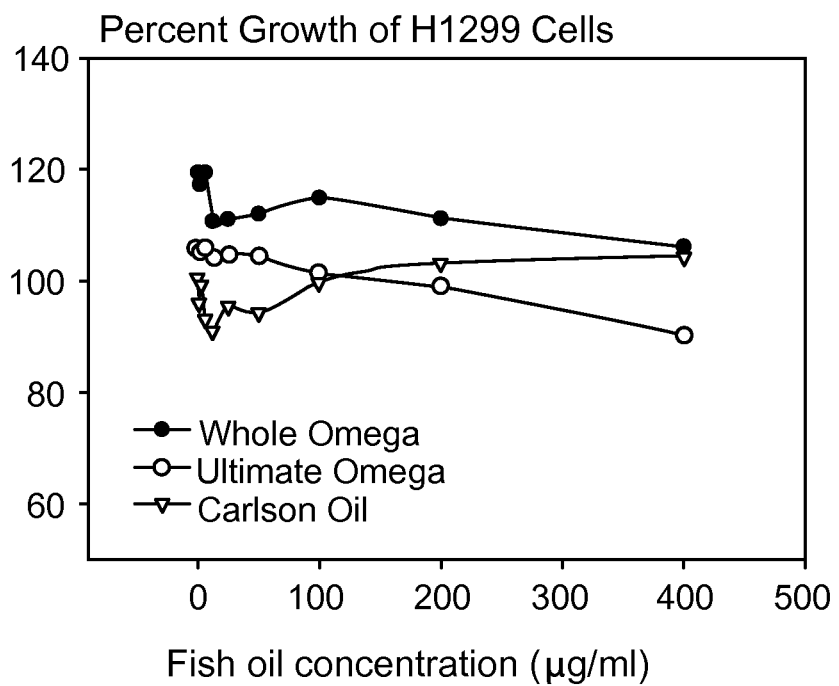

FIG. 17 illustrates the relative effect of WholeMega and two commercial fish oil products to inhibit proliferation of human A549 nonsmall cell lung cancer cells (top figure) and human H1299 nonsmall cell lung cancer cells (bottom figure). A549 cells overexpress COX-2, as many cancer cells are known to do. H1299 cells do not overexpress COX-2, and thus provide a comparative control for cancer cells that do not overexpress COX-2. WholeMega clearly has a more potent effect than the other two products on the A549 cells. In the bottom figure, where the H1299 cells do not overexpress COX-2, the three fish oils showed a similar inhibitory effect on proliferation the cells. The A549 cells over-express COX-2 which normally results in an over-expression/production of PGE2. When provided with an alternate substrate, however, such as fish oil EPA, the resulting product is PGE3 rather than PGE2. This change slows down proliferative capacity hence the drop in proliferation of A549 cells. This more potent effect of WholeMega is surprising and unexpected because all three fish oil compositions tested comprise EPA. The exact mechanism as to why Wholemega is so much more effective than are the other two oils is unknown. Clearly, at least one structural feature unique to the Wholemega composition contributes an additional anti-tumor effect. One possibility is that that other oils in Wholemega (omega-5, omega-7 and omega-9 oils), that are not present in the other two fish oils, contribute to an additional inhibitory effect on the growth of the cancer cells. Another possibility would be the relative fractions of certain oils to one another. Yet another possibility would be the herbal oil component, e.g. SCE rosemary and SCE oregano) contribute an added inhibitory effect on the growth of the cancer cells. Other possible non-limiting mechanisms may also play a role in WholeMega's unexpected ability to inhibit the growth of tumor cells, including tumor cells that overexpress COX-2. In one embodiment, the herbal and polyunsaturated oil composition of the present subject matter inhibits the growth of cancer cells when a therapeutically effective dose is administered to an animal. In one embodiment, the herbal and polyunsaturated oil composition of the present subject matter inhibits the growth of cancer cells which overexpress COX-2.

Figure 18:
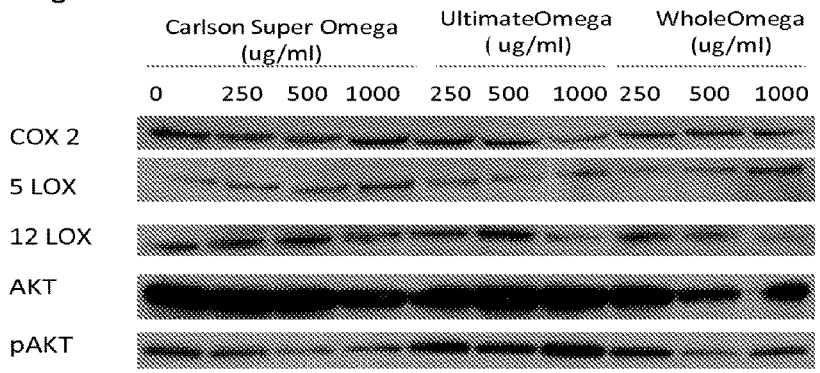
FIG. 18. The effect of WholeMega, UltimateOmega, and Carlson Super fish oil products on expression of COX-2,5- and 12-LOXs and Akt/pAkt in human A549 lung cancer cells. Relevant protein expression was determined by Western blotting and quantified by densitometry for the three fish oil products (FIG. 18 A). Percent change of protein expression at different doses of fish oil are shown for WholeMega (FIG. 18 B) and Carlson's fish oil (FIG. 18 C).
Figure 18:
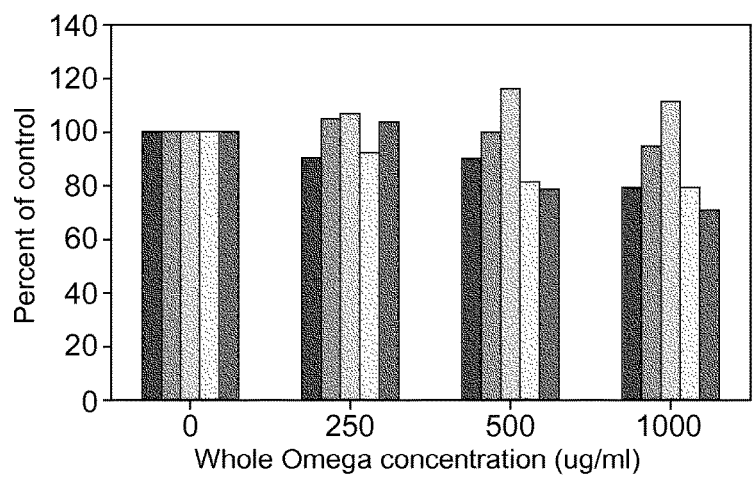
Figure 18:
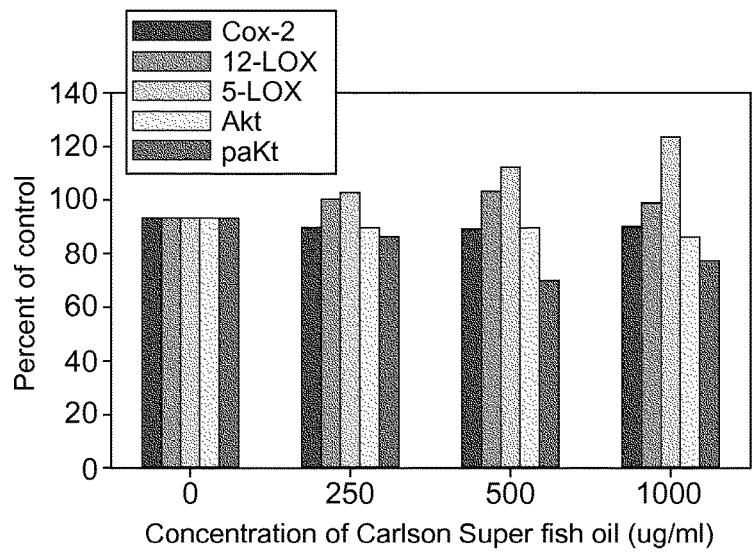

The effect of three fish oil products on alterations of COX and LOX pathways, the effect of these three fish oils on the protein expression of COX-2,5-LOX and 12-LOX in A549 cells was examined. As shown in FIG. 18, the expression of 12-LOX was slightly reduced by 20% and 15% in A549 cells treated with Ultimate Omega and WholeMega (1000 ug/ml), respectively. COX-2 nor 5-LOX protein expression were not altered in A549 cells.

The effect of WholeMega, UltimateOmega, and Carlson Super fish oil products on expression of COX-2,5- and 12-LOXs and Akt/pAkt in human A549 lung cancer cells. Cells ($1 \times 10^6$) were allowed to attach overnight to the tissue culture plate and were then treated for 24 hr with different concentrations of fish oils. Cells were then harvested, lysed and the protein expression were determined by Western Blotting and quantified by densitometry. The data in FIG. 18 indicate that WholeMega did 5 not inhibit the expression of COX-2, or 5-LOX and had only a small inhibition of 12-LOX expression. In contrast, WholeMega (500 ug/ml) inhibited (30%) both Akt and pAkt expression. A similar degree of inhibition was observed in the level of phosphorylated Akt in A549 cells treated with Carlson's fish oil, but not in total Akt. No such effect was observed in A549 cells treated with Ultimate Omega.

Expression of Akt and phosphorylation of Akt was measured in cells treated with three different fish oil products. One of the mechanisms possibly associated with anti-proliferative activity of omega-3 fatty acids is inhibition of total Akt and phosphorylation of Akt. The effect of the three fish oil products on protein levels of Akt and pAkt were measured as a potential molecular mechanism responsible inpart for fish oil induced cell growth inhibition in human lung cancer cell s. As indicated in FIGS. 18 (A and B), the level of total Akt was reduced by 30% in the A549 cells treated with WholeMega. Additionally, WholeMega also inhibited the hosphorylation of Akt as evidenced by reduced expression of pAkt (decrease of 32%) in A549 cells. This inhibitory effect was concentration dependent. In contrast, Carlson Super fish oil only inhibited the phosphorylation of Akt, but not total Akt (FIG. 18 C). No changes in either Akt or pAkt levels were observed in cells treated with similar amounts of Nordic Natural's Ultimate Omega (data not shown) These data suggest that inhibition of Akt pathways could be a partial mechanism responsible for WholeMega's anti-proliferative activity.

Figure 19:
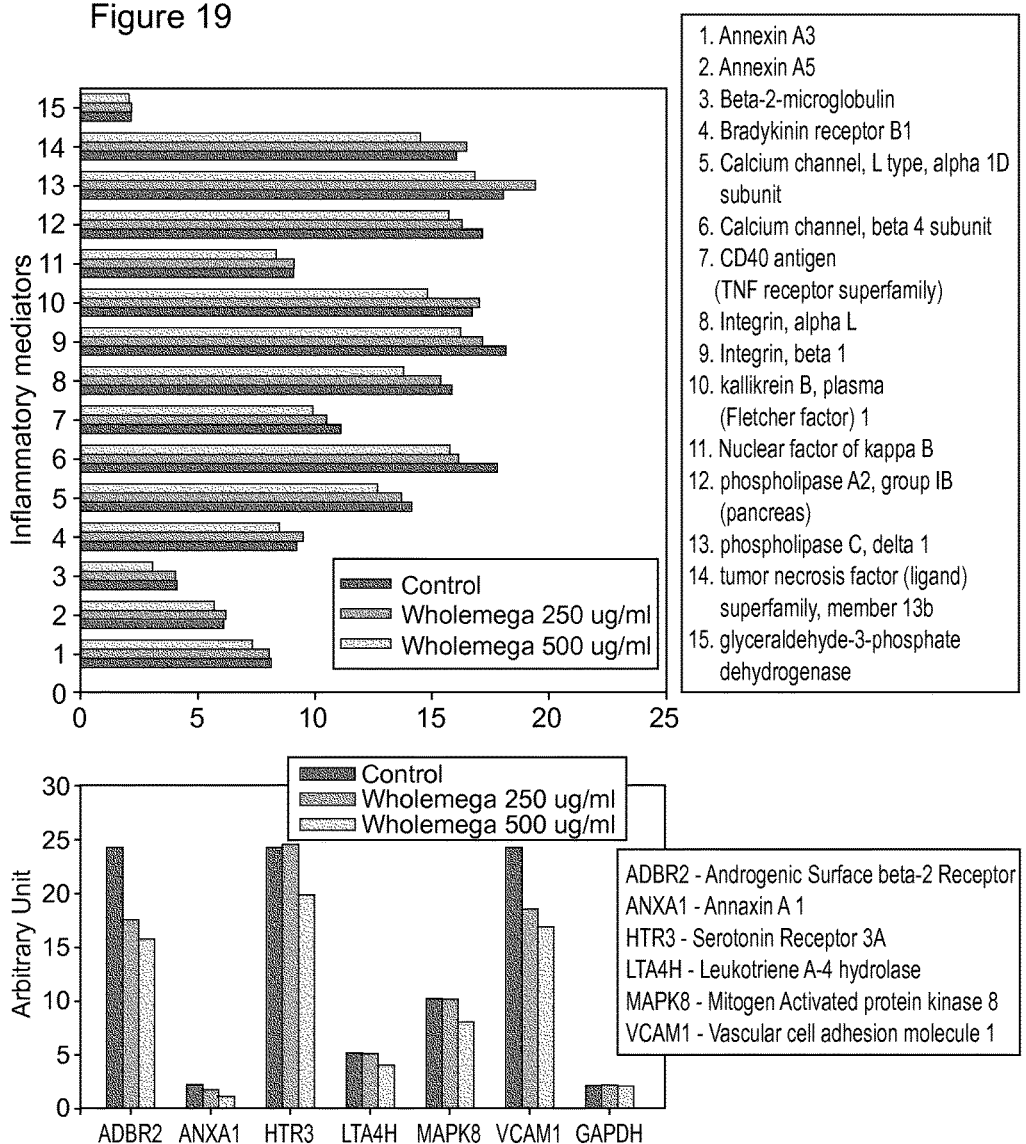
FIG. 19. Inflammation gene array expression in human non-small cell lung cancer A549 cells treated with Wholemega. Those genes that were significantly reduced but by less than 20% are shown in the top figure while those that were reduced to an even greater extent (between 20 to 50%) are shown in the bottom figure.

Example 12: Expression of Inflammatory Genes in RAW Macrophage Cells Treated with Wholemega To further describe how WholeMega may affect inflammatory pathways, the effect of WholeMega on inflammatory cytokines and 5 genes associated with inflammation was examined by inflammation array analyses and real time PCR. Briefly, Cells were plated on 100 mm plates and treated for 24 hrs with WholeMega (250-500 ug/ml) in serum-free conditions. RNA was extracted from the cells using standard Trizol (Invitrogen) following manufacturer's instructions. RNA was then reverse-transcribed using a SuperScript® II First-Strand Synthesis Kit. The cDNA generated was prepared by use of a Taqman Universal PCR Master Mix (Applied Biosystems). An aliquot (100 ul) was loaded into each well of the Inflammation Array Micro Fluidic Card (Applied Biosystems), centrifuged and then sealed. Software for the Inflammation Array was downloaded onto the 7900 HT Fast RealTime PCR System (Applied Biosystems). The card was loaded and Ct values were evaluated as correlates to the relative level of gene expression. As shown in FIG. 19, among 95 inflammation associated genes tested, all annexin genes were down-regulated with strongest inhibition of annexin AI.

The expression of genes responsible for catabolizing the pro-inflammatory product leukotriene LTB4, namely LTA4 hydrolase, was also reduced compared to that of the control group. This is consistent with reduction in enzyme product LTB4 in A549 cells treated with WholeMega (500 ug/ml)

Genes associated with expression of serotonin receptor, MAPKinase and vascular adhesion were also down-regulated more than 20% compared to that of untreated control cells. To confirm whether similar changes occur in a separate macrophage-like cell line, RAW cells were used. Cells were treated as previously described and rat inflammatory gene array (Applied Biosystems) analyses was performed. In comparison to inflammatory associated gene expression in human NSCLC A549 cells, the most affected genes in RAW cells treated with WholeMega were those associated with phospholipase activity. The commonly affected genes by WholeMega in both A549 and Raw cells were Annexin A3, MAPKinase, phospholipase A and C. These data suggest that WholeMega has the ability to down-regulate a series of important inflammation associated genes including leukotriene A4 hydrolase (leukotriene synthesis, A549 cells), Mitogen activated protein kinase (MAPK; cell proliferation), and vascular cell adhesion molecule (VCAM-1) a cell surface glycoprotein which has been implicated in the etiology of malignant disease.

FIG. 19 shows the results of inflammation gene array expression in human non-small cell lung cancer A549 cells treated with Wholemega. Those genes that were reduced by less than 20% with Wholemega treatment are shown in the top figure while those that were reduced to an even greater extent (between 20 to 50%) are shown in the bottom figure. In one embodiment, compositions of the present subject matter may be used to inhibit expression of at least one receptor or enzyme selected from the group consisting of Androgenic Surface beta-2 Receptor (ADBR2), Annaxin A 1 (ANXA1), Serotonin Receptor 3 (HTR3), Leukotriene A-4 hydrolase (LTA4H), Mitogen Activated kinase 8 (MAPK8), Vascular cell adhesion molecule 1 protein (VCAM1), Annexin A3, Annexin AS, Beta-2-microglobulin, Bradykinin receptor B1, Calcium channel L type alpha ID subunit, Calcium channel beta 4 subunit, CD40 antigen (TNF receptor superfamily), Integrin alpha L, integrin beta 1, kallikrein B plasma (Fletcher factor) 1, Nuclear factor of kappa B, phospholipaseA2 group IB (pancreas), phospholipase C delta 1, tumor necrosis factor (ligand) superfamily member 13b, and glyceraldehyde-3-phosphate dehydrogenase. In another embodiment, compositions of the present subject matter may be used to inhibit expression of at least one receptor or enzyme selected from the group consisting expression in human NSCLC A549 cells, the most affected genes in RAW cells treated with WholeMega were those associated with phospholipase activity. The commonly affected genes by WholeMega in both A549 and Raw cells were Annexin A3, MAPKinase, phospholipase A and C. These data suggest that WholeMega has the ability to down-regulate a series of important inflammation associated genes including leukotriene A4 hydrolase (leukotriene synthesis, A549 cells), Mitogen activated protein kinase (MAPK; cell proliferation), and vascular cell adhesion molecule (VCAM-1) a cell surface glycoprotein which has been implicated in the etiology of malignant disease.

FIG. 19 shows the results of inflammation gene array expression in human non-small cell lung cancer A549 cells treated with Wholemega. Those genes that were reduced by less than 20% with Wholemega treatment are shown in the top figure while those that were reduced to an even greater extent (between 20 to 50%) are shown in the bottom figure. In one embodiment, compositions of the present subject matter may be used to inhibit expression of at least one receptor or enzyme selected from the group consisting of Androgenic Surface beta-2 Receptor (ADBR2), Annaxin A 1 (ANXA1), Serotonin Receptor 3 (HTR3), Leukotriene A-4 hydrolase (LTA4H), Mitogen Activated kinase 8 (MAPK8), Vascular cell adhesion molecule 1 protein (VCAM1), Annexin A3, Annexin AS, Beta-2-microglobulin, Bradykinin receptor B1, Calcium channel L type alpha ID subunit, Calcium channel beta 4 subunit, CD40 antigen (TNF receptor superfamily), Integrin alpha L, integrin beta 1, kallikrein B plasma (Fletcher factor)₁, Nuclear factor of kappa B, phospholipaseA2 group IB (pancreas), phospholipase C delta 1, tumor necrosis factor (ligand) superfamily member 13b, and glyceraldehyde-3-phosphate dehydrogenase. In another embodiment, compositions of the present subject matter may be used to inhibit expression of at least one receptor or enzyme selected from the group consisting of Androgenic Surface beta-2 Receptor (ADBR2), Annexin A 1 (ANXA1), Serotonin Receptor 3 (HTR3), Leukotriene A-4 hydrolase (LTA4H), Mitogen Activated protein kinase 8 (MAPK8), and Vascular cell adhesion molecule 1 (VCAM1) In a further embodiment, the level of expression of the at least one receptor or enzyme is reduced from about 3% to about 20%. In yet another embodiment, the level of expression of the at least one receptor or enzyme is reduced by at least about 20%, such as for example by about 20% to about 50%.

FIG. 20 shows the results of inflammation gene array expression in RAW cells treated with WholeMega (250 and 500 ug/ml) as compared to untreated controls. The designation (*) denotes a level of expression reduced by more than 20% due to WholeMega. The expression of receptor or enzymes associated with COX and 5-LOX as well as phospholipase in RAW cells were reduced in comparison to that of untreated control cells.

These data indicate that WholeMega fish oil is unexpectedly superior to two other commercially available fish oil products, Ultimate Omega and Carlson Super Fish oil, as evidenced by (1) the stronger anti-proliferative activity; (2) ability to form anti-proliferative lipid mediator, PGE3 and LTBs in both human NSCLC A549 and rat macrophage Raw cells; and (3) inhibition of both Ala and pAkt proteins in A549 cells. This is particularly interesting because the relative omega-3 fatty acid concentrations in Wholemega are less than that in Ultimate Omega and Carlson Super Fish oil. The data suggest that at least one unique component to Wholemega and which are in refined compositions of the present subject matter may contribute to the anticancer activity of WholeMega. In one embodiment, this at least one unique component in compositions of the present subject matter responsible for these unpredicted effects may be selected from the group consisting of fatty acids, combinations of fatty acids, herbal components, other non-fatty acid nonherbal components, and combinations thereof. Additionally, the inflammation array data further demonstrate the anti-inflammatory activity of compositions of the present subject matter as evidenced by inhibition of a broad range genes associated with inflammation.

In one embodiment, compositions of the present subject matter may be used to inhibit expression of at least one receptor or enzyme selected from the group consisting of alpha-2-macroglobulin, adrenergic receptor beta 2, annexin A3, acidic ribosomal phosphoprotein PO, cysteinyl leukotriene receptor 1, hydroxyprostaglandin dehydrogenase 15, histamine receptor H2, intercellular adhesion molecule 1, interleukin 1 receptor, leukotriene B4 receptor, mitogen activated protein kinase 3, phospholipase A2 group V, phospholipase C beta 2, phospholipase C delta 1, phospholipase C gamma 2, prostaglandin E receptor 3, prostaglandin-endoperoxide synthase 1, and caspase 1. In a preferred embodiment, compositions of the present subject matter may be used to inhibit expression of at least one receptor or enzyme selected from the group consisting of alpha-2-macroglobulin, adrenergic receptor beta 2, acidic ribosomal phosphoprotein PO, histamine receptor H 2, intercellular adhesion molecule 1, and prostaglandin E receptor 3. In another embodiment of this preferred embodiment, two or more, or three or more, or four or more of the receptors and/or enzymes have a level of expression that is reduced by at least 20%. In a further embodiment, the level of expression of the at least one receptor or enzyme is reduced from about 3% to about 20%. In yet another embodiment, the level of expression of the at least one receptor or enzyme is reduced by more than 20%.

REFERENCES

The following literature references are believed to useful to an understanding of the present subject matter in the context of its place in the relevant art. Citation here is not to be construed as an assertion or admission that any reference cited is material to patentability of the present subject matter. Applicants will properly disclose information material to patentability in an Information Disclosure Statement. The content of each reference is hereby incorporated in their entirety.

1. Singh, S, and Aggarwal, transcription factor NF-kappa B (diferuloylmethane) [corrected] J. 25000. B. B. (1995) Activation of is suppressed by curcumin *Biol. Chem.*, 270, 24995
2. Aggarwal, S., Ichikawa, H., Takada, Y., Sandur, S. K., Shishodia, S, and Aggarwal, B. B. (2006) Curcumin (diferuloylmethane) down-regulates expression of cell proliferation and antiapoptotic and metastatic gene products through suppression of I kappa B alpha kinase and Ala activation. *Mol. Pharmacol.*, 69, 195-206.
3. Plummer, S. M., Holloway, K. A., Manson, M. M., Munks, R. J., Kaptein, A., Farrow, S, and Howells, L. (1999) Inhibition of cyclooxygenase 2 expression in colon cells by the chemo preventive agent curcumin involves inhibition of NF kappa B activation via the NIK/IKK signaling complex. *Oncogene*, 18, 6013-6020.
4. Paschka, A. G., Induction of apoptosis by the green tea component Butler, R. and Young, C. Y. in prostate cancer cell lines (–)-epigallocatechin-3-gallate. (1998) *Cancer, Lett,* 130, 1-7.
5. Kim, D. S., Kim, H. R., Woo, E. R., Hong, S. T., Chae, H. J. and Chae, S. W. (2005) Inhibitory effects of rosmarinic acid on adriamycin-induced apoptosis in H9c2 cardiac muscle cells by inhibiting reactive oxygen species and the activations of c-Jun N-terminal kinase and extracellular signal-regulated kinase. *Biochem. Pharmacol.,* 70, 1066-1078.
6. Huang, S. S, and Zheng, R. L. (2005) Rosmarinic acid inhibits angiogenesis and its mechanism of action in vitro. *Cancer Lett.*
7. Shishodia, S., Majumdar, S., Banerjee, S, and Aggarwal, B. B. (2003) Ursolic acid inhibits nuclear factor-kappaB activation induced by carcinogenic agents through suppression of I kappa B alpha kinase and p65 phosphorylation: correlation with down-regulation of cyclooxygenase 2, matrix metalloproteinase 9, and cyclin D1. *Cancer Res.,* 63, 4375-4383.
8. Choi, Y. H., Baek, J. H., Yoo, M. A., Chung, H. Y., Kim, N. D. and Kim, K. W. (2000) Induction of apoptosis by ursolic acid through activation of caspases and down regulation of c-1APs in human prostate epithelial cells. *Int. J. Oncol.,* 17, 565-571.
9. Kim, S. O., Kundu, J. K., Shin, Y. K., Park, J. H., Cho, M. H., Kim, T. Y. and Surh, Y. J. (2005) [6]-Gingerol inhibits COX-2 expression by blocking the activation of p38 MAP kinase and NF-kappaB in phorbol ester-stimulated mouse skin. *Oncogene,* 24, 2558-2567.
10. Atsumi, T., Murakami, Y., Shibuya, K., Tonosaki, K. and Fujisawa, S. (2005) Induction of cytotoxicity and apoptosis and inhibition of cyclooxygenase-2 gene expression, by curcumin and its analog, alpha-disoeugenol. *Anticancer Res.,* 25, 4029-4036.
11. Tjendraputra, E., Tran, V. H., Liu-Brennan, D., Roufogalis, B. D. and Duke, C. C. (2001) Effect of ginger constituents and synthetic analogues on cyclooxygenase-2 enzyme in intact cells. *Bioorg. Chem.,* 29, 156-163.
12. Manna, S. K., Mukhopadhyay, A. and Aggarwal, B. B. (2000) Resveratrol suppresses TNF-induced activation of nuclear transcription factors NF-kappa B, activator protein-1, and apoptosis: potential role of reactive oxygen intermediates and lipid peroxidation. *J. Immunol.,* 164, 6509-6519.
13. Fukuda, K., Hibiya, Y., Mutoh, M., Koshiji, M., Akao, S, and Fujiwara, H. (1999) Inhibition by berberine of cyclooxygenase-2 transcriptional activity in human colon cancer cells. *J. Ethnopharmacol.,* 66, 227-233.
14. Kelrn, M. A., Nair, M. G., Strasburg, G. M. and DeWitt, D. L. (2000) Antioxidant and cyclooxygenase inhibitory phenolic compounds from Ocimum sanctum Linn. *Phytomedicine,* 7, 7-13.
15. Bemis, D. L., Capodice, J. L., Anastasiadis, A. G., Katz, A. E. and Buttyan, R. (2005) Zyflamend, a unique herbal preparation with nonselective COX inhibitory activity, induces apoptosis of prostate cancer cells that lack COX-2 expression. *Nutr. Cancer.,* 52, 202-212.
16. Aggarwal, B. B. (2004) Nuclear factor-kappaB: the enemy within. *Cancer Cell,* 6, 203-208.
17. Anto, R. J., Mukhopadhyay, A., Shishodia, S., Gairola, C. G. and Aggarwal, B. B. (2002) Cigarette smoke condensate activates nuclear transcription factor-kappaB through phosphorylation and degradation of IkappaB (alpha): correlation with induction of cyclooxygenase-2. *Carcinogenesis,* 23, 1511-1518.
18. Bharti, A. C., Takada, Y., Shishodia, S, and Aggarwal, B. B. (2004) Evidence that receptor activator of nuclear factor (NF)-kappaB ligand can suppress cell proliferation and induce apoptosis through activation of a NF-kappa Bindependent and TRAF6-dependent mechanism. *J. Biol. Chem.,* 279, 6065-6076.
19. Takada, Y., Ichikawa, H., Badmaev, v. and Aggarwal, B. B. (2006) Acetyl-11-ketobeta-boswellic acid potentiates apoptosis, inhibits invasion, by suppressing NF-kappaB expression. *J. Immunol.,* 176, and abolishes osteoclastogenesis and NF-kappaB-regulated gene 3127-3140.
20. Chaturvedi, M. M., Mukhopadhyay, A. and Aggarwal, B. B. (2000) Assay for redox-sensitive transcription factor. *Methods Enzymol.,* 319, 585-602.
21. Abu-Amer, Y. and Tondravi, M. M. (1997) NF-kappaB and bone: the breaking point. *Nat. Med.,* 3, 1189-1190.
22. Liotta, L. A., Thorgeirsson, U. P. and Garbisa, S. (1982) Role of collagenases in tumor cell invasion. *Cancer Metastasis Rev.,* 1, 277-288.
23. Van Antwerp, D. J., Martin, S. J., Kafri, T., Green, D. R. and Verma, I. M. (1996) Suppression of TNF-alpha-induced apoptosis by NF-kappaB. *Science,* 274, 787-789.
24. Wang, C. Y., Mayo, M. W. and Baldwin, A. S., Jr. (1996) TNF- and cancer therapy induced apoptosis: potentiation by inhibition of NF-kappaB. *Science,* 274, 784-787.

25. Yamamoto, K., Arakawa, T., Ueda, N. and Yamamoto, S. (1995) Transcriptional roles of nuclear factor kappa B and nuclear factor-interleukin-6 in the tumor necrosis factor alpha dependent induction of cyclooxygenase-2 in MC3T3-E1 cells. *J. Biol. Chem.*, 270, 31315-31320.

26. Esteve, P. O., Chicoine, E., Robledo, O., Aoudjit, F., Descoteaux, A., Potworowski, E. F. and St-Pierre, Y. (2002) Protein kinase C-zeta regulates transcription of the matrix metalloproteinase-9 gene induced by IL-1 and TNF-alpha in glioma cells via NF-kappa B. *J. Biol. Chem.*, 277, 35150-35155.

27. van de Stolpe, A., Caldenhoven, E., Stade, B. G., Koenderman, L., Raaijmakers, J. A., Johnson, J. P. and van der Saag, P. T. (1994) 12-O-tetradecanoylphorbol-13-acetate and tumor necrosis factor alpha-mediated induction of intercellular adhesion molecule-1 is inhibited by dexamethasone. Functional analysis of the human intercellular adhesion molecular-1 promoter. *J. Biol. Chem.*, 269, 6185-6192.

28. Zhu, L., Fukuda, S., Cordis, S., Cordis, G., Das, D. K. and Maulik, Anti-apoptotic protein survivin plays a significant role in tubular morphogenesis of human coronary arteriolar endothelial cells by hypoxic preconditioning. *FEBS Lett.*, 508, 369-374.

29. Chu, Z. L., McKinsey, T. A., Liu, L., Gentry, J. J., Malim, M. H. and Ballard, D. W. (1997) Suppression of tumor necrosis factor-induced cell death by inhibitor of apoptosis cIAP2 is under NF-kappaB control. *Proc. Natl. Acad. Sci. USA.*, 94, 10057-10062.

30. You, M., Ku, P. T., Hrdlickova, R. and Bose, H. R., Jr. (1997) ch-IAP1, a member of the inhibitor-of-apoptosis protein family, is a mediator of the antiapoptotic activity of the v-Rel oncoprotein. *Mol. Cell. Biol.*, 17, 7328-7341.

31. Catz, S. D. and Johnson, J. L. (2001) Transcriptional regulation of bcl-2 by nuclear factor kappa B and its significance in prostate cancer. *Oncogene*, 20, 7342-7351.

32. Stehlik, C., de Martin, R., Kumabashiri, I., Schmid, J. A., Binder, B. R. and Lipp, J. (1998) Nuclear factor (NF) kappaB-regulated X-chromosome-linked iap gene expression protects endothelial cells from tumor necrosis factor alpha-induced apoptosis. *J. Exp. Med.*, 188, 211-216.

33. Tamatani, M., Che, Y. H., Matsuzaki, H., Ogawa, S., Okado, H., Miyake, S., Mizuno, T. and Tohyama, M. (1999) Tumor necrosis factor induces Bcl-2 and Bclx expression through NFkappaB activation in primary hippocampal neurons. *J. Biol. Chem.*, 2 7 4, 8 5 31-8 5 3 8.

34. Schwenzer, R., Siemienski, K., Liptay, S., Schubert, G., Peters, N., Scheurich, P., Schmid, R. M. and Wajant, H. (1999) The human tumor necrosis factor (TNF) receptor-associated factor 1 gene (TRAF1) is up-regulated by cytokines of the TNF ligand family and modulates TNF-induced activation of NF-kappaB and c-Jun N-terminal kinase. *J. Biol. Chem.*, 274, 19368-19374.

35. Kreuz, S., Siegmund, D., Scheurich, P. and Wajant, H. (2001) NF-kappaB inducers upregulate cFLIP, a cycloheximide-sensitive inhibitor of death receptor signaling. *Mol. Cell. Biol.*, 21, 3964-3973.

36. Shishodia, S, and Aggarwal, B. B. (2004) Nuclear factor kappaB activation mediates cellular transformation, proliferation, invasion angiogenesis and metastasis of cancer. *Cancer Treat Res.*, 119, 139-173.

37. Takada, Y., Singh, S, and Aggarwal, B. B. (2004) Identification of a p65 peptide that Selectively inhibits NFkappa B activation induced by various inflammatory stimuli and 10 its role in down-regulation of NF-kappaB-mediated gene expression and up-regulation of apoptosis. *J. Biol. Chem.*, 279, 15096-15104.

The present subject matter being thus described, it will be obvious that the same may be modified or varied in many ways. Such modifications and variations are not to be regarded as a departure from the spirit and scope of the present subject matter and all such modifications and variations are intended to be included within the scope of the following claims.

We claim:

1. A method of maintaining joint health in a mammal, comprising providing the mammal with a composition for oral administration comprising an herbal composition wherein the herbal composition consists of a supercritical extract of rosemary, and a supercritical extract of oregano, wherein the ratio of supercritical extract of rosemary to supercritical extract of oregano is about 1:1.

2. The method of claim 1, wherein the composition is in the form of one or more capsules, tablets, or pills.

3. The method of claim 1, wherein the composition further comprises a carrier.

4. The method of claim 3, wherein the carrier is selected from the group consisting of magnesium carbonate, magnesium stearate, talc, sugar, lactose, pectin, dextrin, starch, gelatin, tragacanth, methylcellulose, sodium carboxymethylcellulose, a low melting wax, cocoa butter, and combinations thereof.

5. The method of claim 3, wherein the carrier comprises gelatin.

6. The method of claim 1, wherein the supercritical extract of rosemary is a supercritical extract of a leaf of rosemary.

7. The method of claim 6, wherein the supercritical extract of oregano is a supercritical extract of a leaf of oregano.

8. The method of claim 1, wherein the supercritical extract of oregano is a supercritical extract of a leaf of oregano.

9. A method of maintaining joint health in a mammal, comprising providing the mammal with a composition comprising an herbal composition wherein the herbal composition consists of from about 0.1 to about 1 wt % supercritical extract of leaf of rosemary, and from about 0.1 to about 1 wt % supercritical extract of oregano.

10. The method of claim 9, wherein the composition comprises a therapeutically effective amount of the supercritical extract of rosemary and extract of oregano to treat inflammation, rheumatoid arthritis, osteoarthritis, or combinations thereof.

11. The method of claim 9, further comprising a carrier selected from the group consisting of magnesium carbonate, magnesium stearate, talc, sugar, lactose, pectin, dextrin, starch, gelatin, tragacanth, methylcellulose, sodium carboxymethylcellulose, a low melting wax, cocoa butter, and combinations thereof.

12. The method of claim 11, wherein the carrier comprises gelatin.

\* \* \* \* \*